US009629899B2

(12) United States Patent
Puri

(10) Patent No.: US 9,629,899 B2
(45) Date of Patent: Apr. 25, 2017

(54) TARGETED CARGO PROTEIN COMBINATION THERAPY

(71) Applicant: The United States of America Department of Health and Human Services, Washington, DC (US)

(72) Inventor: Raj K. Puri, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/812,681

(22) Filed: Jul. 29, 2015

(65) Prior Publication Data

US 2016/0184398 A1 Jun. 30, 2016

Related U.S. Application Data

(63) Continuation of application No. 13/886,034, filed on May 2, 2013, now abandoned, which is a continuation of application No. 12/579,281, filed on Oct. 14, 2009, now abandoned.

(60) Provisional application No. 61/105,408, filed on Oct. 14, 2008.

(51) Int. Cl.
| | |
|---|---|
| *A61K 38/00* | (2006.01) |
| *A61K 39/00* | (2006.01) |
| *A61K 39/395* | (2006.01) |
| *A61K 38/20* | (2006.01) |
| *A61K 31/513* | (2006.01) |
| *A61K 31/519* | (2006.01) |
| *A61K 31/555* | (2006.01) |
| *A61K 31/704* | (2006.01) |
| *A61K 31/7068* | (2006.01) |
| *A61K 33/24* | (2006.01) |
| *A61K 45/06* | (2006.01) |
| *A61K 49/00* | (2006.01) |
| *A61K 47/48* | (2006.01) |

(52) U.S. Cl.
CPC ........ *A61K 38/2026* (2013.01); *A61K 31/513* (2013.01); *A61K 31/519* (2013.01); *A61K 31/555* (2013.01); *A61K 31/704* (2013.01); *A61K 31/7068* (2013.01); *A61K 33/24* (2013.01); *A61K 45/06* (2013.01); *A61K 47/48246* (2013.01); *A61K 49/0008* (2013.01)

(58) Field of Classification Search
None
See application file for complete search history.

(56) References Cited

U.S. PATENT DOCUMENTS

| 6,011,002 A | 1/2000 | Pastan et al. |
|---|---|---|
| 2002/0169154 A1 | 11/2002 | Ruggeri et al. |
| 2005/0227929 A1 | 10/2005 | Masferrer |
| 2011/0171219 A1* | 7/2011 | Merchant ......... A61K 47/48261 424/134.1 |

OTHER PUBLICATIONS

Shimamura et al. (Oct. 17, 2007, Cancer Research 67:9903-9912).*
Abbruzzese, J. et al., Seminars in Oncology, 26(6) Suppl. 20, 1-8, 2002.
Bergers, G. et al., Benefits of Targeting Both Pericytes and Endothelial Cells in the Tumor Vasculature with Kinase Inhibitors, J Clin Invest, 111(9), 1287-1295, 2003.
Bocci, G. et al., Fluvastatin Synergistically Enhances the Antiproliferative Effect of Gemcitabine in Human Pancreatic Cancer MIAPaCa-2 Cells, Br J Cancer, 93, 319-330, 2005.
Burris, H. et al., Improvements in Survival and Clinical Benefit With Gemcitabine as First-Line Therapy for Patients With Advanced Pancreas Cancer: A Randomized Trial, J Clin Oncol, 15(6), 2403-2413, 1997.
Chun, P. et al., Synergistic Effects of Gemcitabine and Gefitinib in the Treatment of Head and Neck Carcinoma, Cancer Res, 66(2), 981-988, 2006.
Debinski, W. et al., Interleukin-4 Receptors Expressed on Tumor Cells May Serve as a Target for Anticancer Therapy Using Chimeric Pseudomonas Exotoxin, Int J Cancer, 58, 744-748, 1994.
Ishige, K. et al., Potent in Vitro and in Vivo Antitumor Activity of Interleukin-4-Conjugated Pseudomonas Exotoxin Against Human Biliary Tract Carcinoma, Int J Cancer, 123, 2915-2922, 2008.
Kawakami, K. et al., Internalization Property of Interleukin-4 Receptor α Chain Increases Cytotoxic Effect of Interleukin-4 Receptor-targeted Cytotoxin in Cancer Cells, Clin Cancer Res, 8, 258-266, 2002.
Kawakami, K. et al., Targeting Interleukin-4 Receptors for Effective Pancreatic Cancer Therapy, Cancer Res, 62, 3575-3580, 2002.
Kim, C. et al., Diphtheria Toxin Fused to Granulocyte-Macrophage Colony-Stimulating Factor and Ara-C Exert Synergistic Toxicity Against Human AML HL-60 Cells, Leukemia Research, 23, 527-538, 1999.
Kornmann, M. et al., Pancreatic Cancer Cells Express Interleukin-13 and -4 Receptors, and Their Growth is Inhibited by Pseudomonas Exotoxin Couples to Interleukin-13 and -4, Anticancer Research, 19, 125-132, 1999.
Leland, R. et al., Human Breast Carcinoma Cells Express Type II IL-4 Receptors and Are Sensitive to Antitumor Activity of a Chimeric IL-4-Pseudomonas Exotoxin Fusion Protein in Vitro and in Vivo, Molecular Medicine, 6(3), 165-178, 2000.
O'Connor, R. et al., Anti-B4-Blocked Ricin Synergizes With Doxorubicin and Etoposide on Multidrug-Resistant and Drug-Sensitive Tumors, Blood, 86(11), 4286-4294, 1995.
Polito, L. et al., The Conjugate Rituximab/Saporin-S6 Completely Inhibits Clonogenic Growth of CD20-Expressing Cells and Produces a Synergistic Toxic Effect with Fludarabine, Leukemia, 18, 1215-1222, 2004.

(Continued)

*Primary Examiner* — Elizabeth C Kemmerer
(74) *Attorney, Agent, or Firm* — Dennis A. Bennett

(57) ABSTRACT

The present invention combines a targeted cargo protein with an active agent for the treatment of a disease or condition.

4 Claims, 6 Drawing Sheets

(56) References Cited

OTHER PUBLICATIONS

Pratesi, G. et al., Therapeutic Synergism of Gemcitabine and CpG-Oligodeoxynucleotides in an Orthotopic Human Pancreatic Carcinoma Xenograft, Cancer Res, 65(14), 6388-6393, 2005.
Prokopchuk, O. et al., Interleukin-4 Enhances Proliferation of Human Pancreatic Cancer Cells: Evidence for Autocrine and Paracrine Actions, Br J Cancer, 92(5), 921-928, 2005.
Symon, Z. et al., Concurrent Chemoradiotherapy with Gemcitabine and Cisplatin for Pancreatic Cancer: From the Laboratory to the Clinic, Int J Radiation Oncol Biol Phys, 53(1), 140-145, 2002.
Tempero, M. et al., Randomized Phase II Comparison of Dose-Intense Gemcitabine: Thirty-Minute Infusion and Fixed Dose Rate Infusion in Patients with Pancreatic Adenocarcinoma, J Clin Oncol, 21(18), 3402-3408, 2003.
Verma, A. et al., Increased Expression of Tissue Transglutaminase in Pancreatic Ductal Adenocarcinoma and Its Implications in Drug Resistance and Metastasis, Cancer Res, 66(21), 10525-10533, 2006.

\* cited by examiner

| IL-4 AAs 38-129 | IL-4 AAs 1-37 | PE AAs 253-364, 381-608 | — KDEL |

D       GGNGG

```
  1   Met Asp Thr Thr Glu Lys Glu Thr Phe Cys Arg Ala Ala Thr Val Leu Arg Gln Phe Tyr
 21   Ser His His Glu Lys Asp Thr Arg Cys Leu Gly Ala Thr Ala Gln Gln Phe His Arg His
 41   Lys Gln Leu Ile Arg Phe Leu Lys Leu Arg Asp Arg Asn Leu Trp Gly Leu Ala Gly Leu
 61   Asn Ser Cys Pro Val Lys Glu Ala Asn Gln Ser Thr Leu Glu Asn Phe Leu Glu Arg Leu
 81   Lys Thr Ile Met Arg Glu Lys Tyr Ser Lys Cys Ser Ser Gly Gly Asn Gly Gly His Lys
101   Cys Asp Ile Thr Leu Gln Glu Ile Ile Lys Thr Leu Asn Ser Leu Thr Glu Gln Lys Thr
121   Leu Cys Thr Glu Leu Thr Val Thr Asp Ile Phe Ala Ala Ser Lys Ala Ser Gly Gly Pro
141   Glu Gly Gly Ser Leu Ala Ala Leu Thr Ala His Gln Ala Cys His Leu Pro Leu Glu Thr
161   Phe Thr Arg His Arg Gln Pro Arg Gly Trp Glu Gln Leu Glu Gln Cys Gly Tyr Pro Val
181   Gln Arg Leu Val Ala Leu Tyr Leu Ala Ala Arg Leu Ser Trp Asn Gln Val Asp Gln Val
201   Ile Arg Asn Ala Leu Ala Ser Pro Gly Ser Gly Gly Asp Leu Gly Glu Ala Ile Arg Glu
221   Gln Pro Glu Gln Ala Arg Leu Ala Leu Thr Leu Ala Ala Ala Glu Ser Glu Arg Phe Val
241   Arg Gln Gly Thr Gly Asn Asp Glu Ala Gly Ala Ala Asn Gly Pro Ala Asp Ser Gly Asp
261   Ala Leu Leu Glu Arg Asn Tyr Pro Thr Gly Ala Glu Phe Leu Gly Asp Gly Gly Asp Val
281   Ser Phe Ser Thr Arg Gly Thr Gln Asn Trp Thr Val Glu Arg Leu Leu Gln Ala His Arg
301   Gln Leu Glu Glu Arg Gly Tyr Val Phe Val Gly Tyr His Gly Thr Phe Leu Glu Ala Ala
321   Gln Ser Ile Val Phe Gly Gly Val Arg Ala Arg Ser Gln Asp Leu Asp Ala Ile Trp Arg
341   Gly Phe Tyr Ile Ala Gly Asp Pro Ala Leu Ala Tyr Gly Tyr Ala Gln Asp Gln Glu Pro
361   Asp Ala Arg Gly Arg Ile Arg Asn Gly Ala Leu Leu Arg Val Tyr Val Pro Arg Ser Ser
381   Leu Pro Gly Phe Tyr Arg Thr Ser Leu Thr Leu Ala Ala Pro Glu Ala Ala Gly Glu Val
401   Glu Arg Leu Ile Gly His Pro Leu Pro Leu Arg Leu Asp Ala Ile Thr Gly Pro Glu Glu
421   Glu Gly Gly Arg Leu Glu Thr Ile Leu Gly Trp Pro Leu Ala Glu Arg Thr Val Val Ile
441   Pro Ser Ala Ile Pro Thr Asp Pro Arg Asn Val Gly Gly Asp Leu Asp Pro Ser Ser Ile
461   Pro Asp Lys Glu Gln Ala Ile Ser Ala Leu Pro Asp Tyr Ala Ser Gln Pro Gly Lys Pro
481   Pro Lys Asp Glu Leu
```

FIG. 1

TARGETED CARGO PROTEIN COMBINATION THERAPY

CROSS REFERENCE TO RELATED APPLICATIONS

This application is a continuation of U.S. application Ser. No. 13/886,034, filed May 2, 2013, now abandoned, which is a continuation of U.S. application Ser. No. 12/579,281, filed Oct. 14, 2009, now abandoned, which claims the benefit of priority of U.S. Provisional Application No. 61/105,408 filed on Oct. 14, 2008, the contents of each are incorporated herein by reference in their entirety.

ACKNOWLEDGMENT OF GOVERNMENT SUPPORT

This invention was created in the performance of a Cooperative Research and Development Agreement with the Food and Drug Administration, an Agency of the Department of Health and Human Services. The Government of the United States has certain rights in this invention.

FIELD

This invention relates to compositions and methods for treating diseases and conditions using targeted cargo proteins in combination with another active agent.

BACKGROUND

Pancreatic ductal adenocarcinoma (PDA) is one of the most lethal human malignancies (32,000 deaths per year). Because of its aggressive growth and rapid metastasis to lymph nodes and liver, only 10% to 15% of patients are found to be resectable at diagnosis (1). Currently, the most common strategy for the treatment of advanced pancreatic cancer is treatment with gemcitabine, although the median survival time continues to be <6 months for these patients (2, 3). Recently, several types of inhibitors targeting the epidermal growth factor (EGF) receptor, platelet-derived growth factor (PDGF) receptor, and nuclear factor-nB (NF-nB) have shown their effectiveness in pancreatic cancer in murine models (4-7). In clinical trials, EGF receptor tyrosine kinase inhibitor (Erlotinib, Tarceva) plus gemcitabine enhances 1-year survival for patients with advanced pancreatic cancer (8). However, the difference in median survival between Erlotinib plus gemcitabine group and gemcitabine alone group is <1 month. An effective new approach is needed for management of patients with this disease.

Gemcitabine (Gemzar) is a widely accepted first-line therapy for advanced pancreatic cancer, although the median survival time continues to be <6 months for these patients (2, 3). As most studies using single agent show low response rate and little effect on patient survival in advanced adenocarcinoma, several clinical trials using a combined approach of radiotherapy and/or molecular target therapy with gemcitabine have been initiated (33). In vitro studies have reported synergistic effect of gemcitabine with cisplatin, fluvastatin hydroxymethylglutaryl-CoA reductase inhibitor, CpG-oligodeoxynucleotides, EGFR, PDGF, and vascular endothelial growth factor inhibitor targeting drugs (6, 34-37). In addition, immunotoxins were shown to exert synergistic effect with chemotherapeutic drugs, for example, doxorubicin plus anti-B4-blocked ricin, Ara-C plus granulocyte macrophage colony-stimulating factor fused to truncated diphtheria toxin (DT388-GM-CSF), and fludarabine with rituximab saporin-S6 conjugated protein (38-40).

SUMMARY

The disclosure describes proteins and other moieties that interact or bind to target cells such as cancer cells using a targeting moiety that is linked to a protein or other toxic agent that kills or inhibits growth or function of the target cells. The protein or other toxic agent that kills or inhibits cancer cell growth is referred to as a cargo moiety and the cargo moiety linked to the targeting moiety is collectively referred to as a targeted cargo protein. As described herein, these targeted cargo proteins are used in combination with active agents know to be effective in treating cancer to synergistically enhance the treatment of cancer in a mammalian subject, such as a human. The active agents used in combination with the targeted cargo proteins may be chemotherapeutic agents, antibodies or other agents typically used to treat cancer or other diseases or conditions. Targeting cell surface receptors with targeted cargo proteins provides a unique opportunity for tumor therapy.

The invention is based in part on the unexpected discovery that a targeted cargo protein targeted against the IL-4 receptor, interleukin-4 (IL-4) cytotoxin (an embodiment of which is also known as PRX321), when combined with gemcitabine, a chemotherapeutic agent currently used to treat advanced pancreatic cancer, is shown to have a synergistic anti-tumor effect both in vitro and in a clinically relevant mouse model of advanced pancreatic cancer. Specifically, those mice treated with a combination of PRX321 and gemcitabine showed a significant decrease in tumor burden and improved survival compared to treatment with either PRX321 or gemcitabine alone. This study demonstrates for the first time the potential of combining an IL-4 cytotoxin such as PRX321 with a chemotherapeutic agent for treating patients with pancreatic cancer. The devices and methods of the present invention are directed to alleviating the above-described problems with previous treatments and, in addition, provide improved therapeutic results in comparison to IL-4-cytotoxin (IL4-PE) alone. It is believed that unique target expression on PDA and synergistic effect of two drugs having independent mechanisms of action contribute to the overall improved therapeutic results.

Here, we show the efficacy of the combination therapy of gemcitabine with PRX321 in animal models of pancreatic ductal adenocarcinoma (PDA). Targeting cell surface receptor with targeted cargo proteins (e.g. cytotoxins or immunotoxins) provides a unique opportunity for tumor therapy. Targeted cargo proteins offer the advantage of enhanced specificity and direct toxicity for tumor cells that overexpress the receptor, thus limiting the potential toxicity to normal tissues (9). Several clinical trials using PRX321, IL-13 cytotoxin, and recombinant immunotoxin BL22 have shown survival benefits in patients with glioblastoma multiforme, chronic lymphocytic leukemia, and hairy cell leukemia (10-13).

Interleukin-4 (IL-4) is an important Th2-derived cytokine, which is involved in mediating antitumor immune-modulating activities (14). IL-4 has been shown to have a modest but direct inhibitory effect on the growth of several tumor cells in vitro and in vivo (15, 16). Based on these properties, IL-4 was tested in the clinic as a treatment for hematopoietic and solid malignancies, but it showed limited antitumor activity (17). To improve this limited activity, we targeted IL-4 receptor (IL-4R) because a variety of human tumor cells, including pancreatic cancer, express high-affinity receptors for IL-4 (18-22).

We show herein that 60% of PDA samples express moderate- to high density surface IL-4Rs, whereas normal pancreas express no or very low levels of IL-4R. PRX321 is highly cytotoxic to pancreatic cancer cell lines; however, it was not cytotoxic to HPDE cells, fibroblasts, and HUVEC, which express no or low levels of IL-4R. We also show that PRX321 synergizes with gemcitabine in mediating cytotoxic activity in pancreatic cancer cell lines in vitro, and in animal models of human pancreatic cancer in vivo. A significant prolonged survival effect of PRX321 and its combination with gemcitabine was shown in mice with early disease. Forty percent of mice that received combination therapy showed complete eradication of pancreatic tumors. In addition, this significant survival benefit was also confirmed in animals implanted with the clinical pancreatic cancer sample.

The foregoing and other features of the disclosure will become more apparent from the following detailed description, which proceeds with reference to the accompanying figures.

BRIEF DESCRIPTION OF THE DRAWINGS

FIG. 1 shows a schematic representation of the structure and amino acid sequence of an exemplary targeted cargo protein, a circularly permuted IL-4-*Pseudomonas* toxin, PRX321 (SEQ ID NO: 1). Disulfide bonds are indicated on the drawing.

DETAILED DESCRIPTION

Figure 2A:
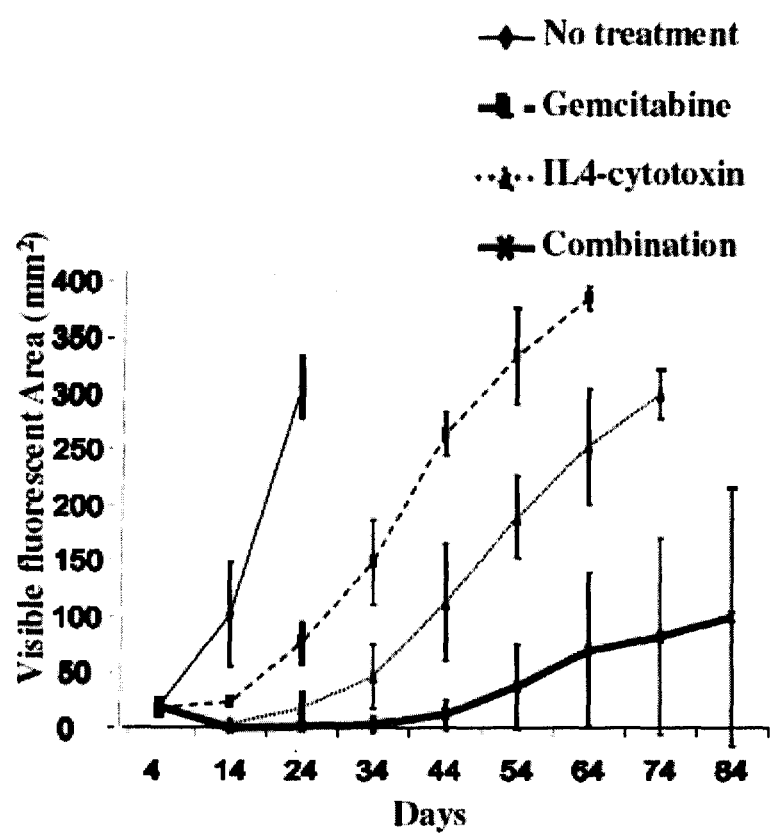
FIG. 2A shows the visible fluorescent area quantification of tumor size as a function of time (obtained from sequential whole-body imaging) in an early pancreatic tumor model in which tumor bearing mice received no treatment, treatment with gemcitabine alone, treatment with IL-4 cytotoxin (PRX321) alone, or a combination of gemcitabine and PRX321.

While the invention has been described in some detail by way of illustration and example, it should be understood that the invention is susceptible to various modifications and alternative forms, and is not restricted to the specific embodiments set forth in the Examples. It should be understood that these specific embodiments are not intended to limit the invention but, on the contrary, the intention is to cover all modifications, equivalents, and alternatives falling within the spirit and scope of the invention.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The present invention involves treating a disease or condition in a subject by administering to the subject at least one targeted cargo protein of the present invention in combination with an active agent known to be effective in treating the disease or condition.

In some embodiments of the invention, the targeted cargo protein comprises a toxin, and is thus a cytotoxin or immunotoxin. Preferably, the targeted cargo protein is a cytotoxin or immunotoxin that binds specifically to the IL-4 receptor, for example, an IL-4-cytotoxin such as PRX321.

In accordance with the present invention, the active agent may be any substance or the like, or treatment protocol or the like, that provides a therapeutic benefit to the patient when combined with the administration of a targeted cargo protein. Active agents include, but are not limited to chemotherapeutic agents. It is intended that an active agent may be a substance that uses a different mechanism of action than the targeted cargo protein, or it may be a substance that uses the same mechanism of action.

In some embodiments of the invention, the active agent is a chemotherapeutic agent. In most preferred embodiments of the invention, the active agent is gemcitabine or doxarubicin.

In some embodiments of the invention, the disease or condition is any disease or condition characterized by cells having a unique or identifying expression pattern of a surface molecule or target. In some embodiments of the invention, the cell surface molecule is a receptor. In some preferred embodiments of the invention, the receptor is an IL-4 receptor (IL-4 R).

Although the IL-4 R is expressed at low levels by certain normal cells, such as resting T lymphocytes, B lymphocytes and resting or activated CD 34 bone marrow cells, it is over-expressed in a wide range of solid tumors, including, for example, brain cancer, including malignant astrocytoma and gliobastoma multiforme, Kaposi sarcoma, bladder cancer, renal cell cancer, breast cancer, pancreatic cancer, non-small cell lung cancer, thyroid cancer, squamous cell carcinoma of the head and neck, colon cancer and other cancers of the gastrointestinal system, mesothelioma and prostate cancer. As used herein, when a cell surface molecule is over-expressed or uniquely expressed in cells characterizing a disease or condition such as cancer, a targeted cargo protein that binds specifically to the cell surface molecule is said to be specific for the cell associated with the disease or condition.

In some embodiments of the invention, the disease or condition is a cancer or tumor producing disease. In some embodiments of the invention, the cancer is a pancreatic cancer. In preferred embodiments of the invention, the pancreatic cancer is pancreatic ductal adenocarcinoma (PDA). In other preferred embodiments of the invention, the disease or condition is any disease or condition that over-expresses IL-4 receptors. Conditions, as used herein, include, but are not limited to inflammation.

In some embodiments, the invention provides methods and compositions for inhibiting the growth of a target cell, said target cell comprising a cell characterized by having over-expression of an IL-4 receptor. The invention includes contacting the cell with a targeted cargo protein, said targeted cargo protein comprising a targeting moiety and a protein synthesis-inhibiting moiety, and then, within a pre-determined and medically appropriate time period (e.g., one week), at least one active agent. In some embodiments of the invention, the pre-determined time period may be selected from the time periods consisting of within 96 hours, within 72 hours, within 48 hours, and within 24 hours. In some embodiments, the cell is concurrently contacted with both the targeted cargo protein and the first active agent.

The present invention also includes a method of treating a disease or condition by administering a targeted cargo protein in combination with an active agent.

As used herein, "in combination" or variations on that phrase, refer to administering the targeted cargo protein and the active agent within a close enough time period that the patient derives a beneficial result that would not have occurred if the targeted cargo protein and the active agent were not administered in combination. In some embodiments of the invention, in combination refers to administering the targeted cargo protein and the active agent in the same composition; in other embodiments the targeted cargo protein and the active agent are administered sequentially or serially. In some embodiments of the invention, the targeted cargo protein and the active agent are administered are part of an integrated therapeutic plan. In some of these exemplary embodiments, the targeted cargo protein and the active agent may be administered hours or days, weeks, or months apart, but the combination of the two agents provides a beneficial result for the patient.

The composition of the present invention may also be administered repetitively. For example, a cargo protein may administered alone or in combination with an active agent, then the cargo protein may be administered again, alone or in combination with an active agent, at any therapeutically appropriate interval (e.g., the next day or after a week).

One skilled in the art will recognize that the invention as described here may be reconfigured into different combinations, elements, and processes which are included within the scope of the invention.

It is possible to deliver IL4-PE through drug leaching stents for localized cancer to avoid systemic exposure and stent serve as a "reservoir"

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a targeted cargo protein" includes single or plural targeted cargo proteins and is considered equivalent to the phrase "comprising at least about one targeted cargo protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

(A) Active agent, as used herein, refers to any substance that provides a therapeutic benefit to the patient. Active agents include but is not limited to chemotherapeutic agents; anti-disease drugs; anti-disease chemicals, immune system mediators, including enhancers and inhibitors; immune suppressive compounds such as cyclosporine and retinoic acid which has shown to enhance the cytotoxic activity of ricin A. Other therapeutic agents include toxins which are not required to be internalized into the target cell such as PRX302 which acts on the cell surface by creating pores.

Exemplary active agents include but are not limited to those disclosed in PCT/US2008/002747 (Pastan, et al.), incorporated herein by reference. The preferred active agents are gemcitabine and doxorubicin. Some additional exemplary active agents are protein synthesis inhibitors such as L-asparaginase, cyctotoxic/antitumor antibiotics, such as daunorubicin, dosorubicin epirubicin, idarubicin, mitoxantrone, valrubicin, bleomycin, hyroxyurea, and mitomycin. Other active agents include plant alkaloids, such as docetaxel, paclitaxel, vinblastine, vincristine, vindesine, and vinorelbine. Other active agents include alkylating agents, such as nitrogen mustards (such as chlorambucil, chlormethine, cyclophosphamide, ifosfamide or melphalan), a nitrosoureas (such as carmustine, lomustine, spreptozocin), platinum drugs (such as carboplatin, cisplatin, oxaliplatin, BBR3464), busulfan, dacarbazine, mechlorethamne, procarbazine, temozolomide, thioTEPA, uramustine), antimetabolites (such as aminopterin, methotrexate, pemetrexed, raltitrexed, cladribine, clofarabine, fludarabine, mercaptopurine, thioguanine, pentostatin, capecitabine, cytarabine, fluorouracil and gemcitabine). Other active also include topoisomerase inhibitors such as topotecan, irinotecan, *podophyllum*, etoposide and teniposide. Active agents also include therapeutic antibodies (such as alemtuzumab, bevacizumab, cetuximab, gentuzumab, pantitumumab, rituximab, tositmomab) and kinase inhibitors (such as imatinib, nilotinib, dasatinib, erlotinib, gefitinib, lapatinib, sorafenib, sunitinib and vandetanib).

Combinations of active agents may be used in the methods of the invention. For example the FOLFOX protocol, which involves administration of three agents, folinic acid, fluorouracil and oxaliplatin, may be used in combination with one or more targeted cargo proteins.

Adjuvants or immune-stimulants such as BCG (*Bacillus* Calmette Geurin) may also be used in combination with targeted cargo proteins.

(B) "Over-expresses" or similar terms, refers to the presence of a receptor, or the presence of a receptor in an amount significantly higher than normal. Typically, such over-expression is an indicator of a disease or condition. I1-4 receptor is one known example. EGFR and VEGFR receptors may also be targeted, in accordance with the present invention.

(C) Targeted cargo protein consists of a targeting moiety linked to a cargo moiety. In accordance with the present invention, a targeting moiety is any compound that binds to a molecule (herein referred to as a target) displayed on the target cell surface. A targeting moiety can be an antibody that binds to a target (e.g. receptor), a ligand (e.g., cytokine or growth factor) that bind to a receptor, a permuted ligand that binds to a receptor or a peptide sequence sensitive to cleavage by a tumor-associated protease. Exemplary targeting moieties include but are not limited to those disclosed in U.S. Pat. No. 6,011,002, incorporated herein by reference. Some exemplary targeting moieties and exemplary GenBank accession numbers are shown in Table 1 below. Typically, targeting moieties selectively bind to one type of cell displaying a target more effectively than they bind to other types of cell that do not display the target, or that display the target at low levels.

TABLE 1

Exemplary targeting moiety sequences

| Receptor or Antigen to be Targeted | Accession Number* |
|---|---|
| Epidermal growth factor (EGF) | NP_001954; EAX06257.1; AAR84237.1 |
| Vascular endothelial growth factor (VEGF) | AAA35789; CAC19515 |
| Interleukin 2 (IL-2) | CAA07317; AAB46883.1; NP_000577.2 |
| Interleukin 3 (IL-3) | AAC08706.1; AAA99502.1; CAE45598.1 |
| Interleukin 4 (IL-4) | AAH70123; CAA57444.1; AAH67515.1 (also see SEQ ID NO: 2 and various circularly permuted ligands in U.S. Pat. No. 6,011,002) |
| IL-5 | NP_000870.1; CAA01794.1; P32927.2 |
| IL-13 | AAH96141.2; AAH96138.1; AAH96139.1 |
| Granuclocyte-macrophage colony stimulating factor (GMCSF) | P04141.1; AAI13925.1; AAI08725.1 |
| Granulocyte colony stimulating factor (GCSF) | Q99062; P09919 |
| Tenascin | AAA36728.1; CAA39628.1; NP_002151.2 |
| Mesothelin | CAC37289.1; ABW03459.1; AAH09272.1; AAH03512.1; as well as the mesothelins disclosed in U.S. Pat. Nos. 7,081,518 and 6,051,405 (mesothelin sequences therein herein incorporated by reference) |
| CD22 | BAA36575.1; BAA36576.1; BAA36567.1 |
| PSMA (also known as folate hydrolase) | ABO93402.2; AAC83972.1; NP_001014986.1; NP_004467.1 |

*GenBank Numbers are herein incorporated by reference, as well as their corresponding nucleic acid sequences.

The cargo moiety may be derived from plant, animal, or bacteria. In accordance with the present invention, cargo moieties function to significantly kill, reduce or inhibit the growth of target cells. A cargo moiety may be a peptide (e.g. protein fragment or full length protein) or other molecule that can function to significantly reduce or inhibit a target cell. In some examples, the cargo moiety is not a peptide, but another molecule that can function to significantly reduce or inhibit the growth of target cells, such as thapsigargin. Exemplary cargo moieties include cytotoxins, such as Pseudomonas exotoxin (PE), diphtheria toxin (DT), including but are not limited to those disclosed in PCT/US2008/002747 (Pastan, et al.), incorporated herein by reference. In other examples, cargo moieties are proteins that normally contribute to the control of cell life cycles, for example a cargo protein can trigger cell death, such as via apoptotic pathways (e.g. Bad, Bax and other pro-apoptotic members of the Bcl-2 family of proteins). Some exemplary cargo moieties and exemplary GenBank accession numbers are provided in Table 2 below.

TABLE 2

Exemplary cargo moiety sequences

| Cargo Moiety | Accession Numbers |
|---|---|
| Diphtheria toxin (DT) | ABU25232; CAA24778 |
| Aerolysin | ABR14715.1; ABR14714.1 |
| Proaerolysin | AAA21938.1; P09167.2; U.S. Pat. No. 7,282,476 (proaerolysin sequences therein herein incorporated by reference) |
| Bouganin | AAL35962 and SEQ ID NO: 9 in U.S. Pat. No. 6,737,511, as well as variant sequences provided in U.S. Pat. No. 7,339,031 and WO 2005/090579 (bouganin sequences therein herein incorporated by reference) |
| *Pseudomonas* exotoxin (PE) | 1IKP A; AAB59097.1; AAF90003.1 (also see SEQ ID NO: 1 of U.S. Pat. No. 6,011,002) |
| Bcl-2 pro-apoptotic proteins such as BAD and BAX | BAD: CAG46757; AAH01901.1; CAG46733.1; and sequences provided in U.S. Pat. No. 6,737,511<br>BAX: CAE52909.1; AAO22992.1; EAW52418.1 |
| Cholera toxin | BAA06291.1; ACF35010.1; BAA06288.1; as well as variant sequences provided in U.S. patent application No. 61/058,872 (variant cholera toxin sequences therein herein incorporated by reference) |
| Ribonuclease A | BAA05124.1; NP_937877.1; NP_115961.2; Q5GAN4.1; and sequences provided in PCT Publication No. WO 2007/041361 (rapLR1 sequences therein herein incorporated by reference) |

*GenBank Numbers are herein incorporated by reference, as well as their corresponding nucleic acid sequences.

In addition to native targeting moieties and cargo moieties, variant sequences can also be used, such as mutant sequences with greater biological activity than that of the native sequence.

The preferred targeted cargo proteins are IL-4-PE, IL-4-BAD, IL-4-DT and IL-4-doxarubicin.

(D) Inhibiting or inhibition or similar terms refers to cell killing, cell inhibition, loss of cell function, or any other action, direct or indirect, that results in or mediates cell viability and/or function. In preferred embodiments, the compositions of the invention include at least two different mechanisms of action, e.g., two mechanisms of cell killing (such as apoptosis and necrosis).

(E) Contacting refers to placement in direct physical association. With respect to therapeutic targeted cargo proteins and active agents, such therapeutics are considered to contact a target cancer cell, such as a pancreatic cancer cell, in a subject if the therapeutics are administered to the subject by a route that is generally accepted in the art for administering that type of therapeutic.

(F) Specific or specific binding refers to a preferential binding between an agent and a specific target. For example, specific binding refers to the situation when a targeted cargo protein that includes a targeting moiety specific for a molecule or receptor displayed on a cancer cell binds to the cancer cell but does not significantly bind to other cells that do not display the target but are in close proximity to the cancer cell. Specific binding interactions are mediated by one or, typically, more noncovalent bonds between the binding molecules. In contrast to non-specific binding sites, specific binding sites are saturable. One exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases under these conditions, the amount of the first binding partner bound will saturate. In another contrast to non-specific binding sites specific binding partners involved in a direct association with each other (e.g., a protein-protein interaction) can be competitively removed (or displaced) from such association (e.g., protein complex) by excess amounts of either specific binding partner. Such competition assays are very well known in the art. If a targeted cargo protein exhibits specific binding to a cell surface molecule on a cancer cell, it is said to be specific for its target on the cancer cell.

(G) Antibody or antibodies refer to Immunoglobulin molecules and immunologically active portions of immunoglobulin molecules, that is, molecules that contain an antigen binding site that specifically binds (immunoreacts with) an epitope, such as an epitope displayed by cancer cells or another target cell. Antibodies include monoclonal antibodies, polyclonal antibodies, as well as humanized antibodies. Antibodies also include affibodies. Affibodies mimic monoclonal antibodies in function but are based on Protein A. Affibodies can be engineered as high-affinity ligands for binding to a targeting moiety.

(H) Subject refers to a living multi-cellular vertebrate organisms, including human a non-human mammal.

Description of exemplary embodiments of targeting moieties and cargo moieties and their combinations that are useful in the methods of the invention are the following:

Targeting Moieties

In addition to the targeting moieties described above, it will be appreciated that targeting moieties (as well as protein-based cargo moieties) may be truncated or modified and still have the same or even more biological activity. Therefore, the invention includes variants of targeting moieties and cargo moieties and portions, fragments or subunits thereof that have at least 60% sequence identity, at least 75%, at least 80%, at least 85%, at least 90%, at least 98%, or even at least 99% sequence identity to the native protein sequences or fragments from which they are derived, as long as the variants retain, or have enhanced, desired biological activity. In some examples, variant sequences retain substantially the same amount of even more of the native biological function of the parent protein, such as the ability to activate an intracellular signal cascade. However, useful variant targeting moiety molecules may in some examples retain little or no biological activity, but retain the ability to bind the appropriate target with high specificity, and such molecules are included within the scope of the invention.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN can be used to compare nucleic acid sequences, while BLASTP can be used to compare amino acid sequences. To compare two nucleic acid sequences, the options can be set as follows: −i is set to a file containing the first nucleic acid sequence to be compared (such as C:\seq1.txt); −j is set to a file containing the second nucleic acid sequence to be compared (such as C:\seq2.txt); −p is set to blastn; −o is set to any desired file name (such as C:\output.txt); −q is set to −1; −r is set to 2; and all other options are left at their default setting. For example, the following command can be used to generate an output file containing a comparison between two sequences: C:\Bl2seq −i c:\seq1.txt −j c:\seq2.txt −p blastn −o c:\output.txt −q −1 −r 2.

To compare two amino acid sequences, the options of Bl2seq can be set as follows: −i is set to a file containing the first amino acid sequence to be compared (such as C:\seq1.txt); −j is set to a file containing the second amino acid sequence to be compared (such as C:\seq2.txt); −p is set to blastp; −o is set to any desired file name (such as C:\output.txt); and all other options are left at their default setting. For example, the following command can be used to generate an output file containing a comparison between two amino acid sequences: C: \Bl2seq −i c:\seq1.txt −j c:\seq2.txt −p blastp −o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a cargo protein or targeting moiety provided herein.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity to a cargo moiety or targeting moiety provided herein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

Antibodies or fragments thereof may be used as targeting moieties. A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the VL, VH, CL and CH1 domains; (ii) an Fd fragment consisting of the VH and CH1 domains; (iii) an Fv fragment consisting of the VL and VH domains of a single arm of an antibody (scFv) and scFv molecules linked to each other to form a bivalent dimer (diabody) or trivalent trimer (triabody); (iv) a dAb fragment (Ward et al., Nature 341:544-546, 1989) which consists of a VH domain; (v) an isolated complimentarity determining region (CDR); and (vi) a F(ab')2 fragment, a bivalent fragment comprising two Fab fragments linked by a disulfide bridge at the hinge region.

Methods of producing polyclonal and monoclonal antibodies are known to those of ordinary skill in the art, and many antibodies are available. See, e.g., Coligan, Current Protocols in Immunology Wiley/Greene, N Y, 1991; and Harlow and Lane, Antibodies: A Laboratory Manual Cold Spring Harbor Press, N Y, 1989; Stites et al., (eds.) Basic and Clinical Immunology (4th ed.) Lange Medical Publications, Los Altos, Calif., and references cited therein; Goding, Monoclonal Antibodies: Principles and Practice (2d ed.) Academic Press, New York, N.Y., 1986; and Kohler and Milstein, Nature 256: 495-497, 1975. Other suitable techniques for antibody preparation include selection of libraries of recombinant antibodies in phage or similar vectors. See, Huse et al., Science 246: 1275-1281, 1989; and Ward et al., Nature 341: 544-546, 1989.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., Nature 298:286, 1982; Morrison, J. Immunol. 123: 793, 1979; Morrison et al., Ann Rev. Immunol 2:239, 1984). Detailed methods for preparation of chimeric (humanized) antibodies can be found in U.S. Pat. No. 5,482,856. Additional details on humanization and other antibody production and engineering techniques can be found in Borrebaeck (ed), Antibody Engineering, 2nd Edition Freeman and Company, N Y, 1995; McCafferty et al., Antibody Engineering, A Practical Approach, IRL at Oxford Press, Oxford, England, 1996, and Paul Antibody Engineering Protocols Humana Press, Towata, N J, 1995.

In some examples, an antibody specifically binds to a target protein (e.g., a cell surface receptor such as an IL4 receptor) with a binding constant that is at least $10^3$ $M^{-1}$ greater, $10^4$ $M^{-1}$ greater or $10^5$ $M^{-1}$ greater than a binding constant for other molecules in a sample. In some examples, a specific binding reagent (such as an antibody (e.g., monoclonal antibody) or fragments thereof) has an equilibrium constant ($K_d$) of 1 nM or less. For example, a specific binding agent may bind to a target protein with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M. Kd values can, for example, be determined by competitive ELISA (enzyme-linked immunosorbent assay) or using a surface-plasmon resonance device such as the Biacore T100, which is available from Biacore, Inc., Piscataway, N.J.

IL-4 is a pleiotropic cytokine produced by activated T cells, and is the ligand for the IL-4 receptor. The IL-4 receptor also binds to IL-13. Thus, IL-13 can also be used as a targeting moiety to target the IL-4 receptor. IL-4, IL-3, IL-5, IL-13, and CSF2 form a cytokine gene cluster on human chromosome 5q, with this gene particularly close to IL-13. Exemplary IL-4 and IL-13 proteins that can be used in the targeted cargo proteins of the present disclosure include those provided in Table 1, as well as sequences having at least 60% sequence identity, at least 75%, at least 80%, at least 85%, at least 90%, at least 95%, at least 98% or even at least 99% sequence identity to such sequences, as long as the variant retains the ability to bind the IL-4 receptor.

IL-4 (including IL-4 circularly permuted ligands and other IL-4 receptor binding proteins such as IL-13) are targeting moieties that can be linked to BCL-2 family proteins, such as BAX, BAD, BAT, BAK, BIK, BOK, BID BIM, BMF and BOK, or a toxin such as aerolysin, proaerolysin, *Pseudomonas* exotoxin, or combinations thereof. Any form or derivative of IL-4 can be used as the targeting moiety. For example, IL-4 or fragments of IL-4 that bind to the IL-4 receptor can be used. Additionally, multiple cargo moieties can be linked to IL-4 or multiple IL-4 proteins can be linked to cargo moieties.

Antibodies (including fragments, humanized antibodies and the like as described above) that specifically bind to IL-4 receptors can be linked to BCL-2 family proteins, such as BAX, BAD, BAT, BAK, BIK, BOK, BID BIM, BMF and BOK, or a toxin such as aerolysin, proaerolysin, *Pseudomonas* exotoxin, or combinations thereof. Antibodies are commercially available from various companies such as Millipore, Bedford, Mass. or custom made antibodies can be ordered from companies such as Cambridge Research Biochemicals.

Cargo Moieties Cargo moieties that are useful in the methods of the invention reduce or inhibit target cells. As described above, some examples of cargo moieties are not proteins, but other molecules, such as chemotherapeutic agents. For example, toxins and proteins that function to control cell life cycles can be used as cargo moieties. Toxins that can be used as cargo moieties include toxins made by microorganisms, plants or animals, as well as toxins made by human cells. Similarly, any natural cell growth controlling protein can be used as a cargo moiety. For example, proteins that trigger cell death during the normal life cycle of an organism can be used as cargo moieties. In some examples, an oncolytic virus (e.g., see Allen et al., *Mol. Ther.* 16:1556-64, 2008) or liposomes carrying cytotoxic agents (e.g., see Madhankumar et al., *Mol. Cancer. Ther.* 5:3162-9, 2006) is used as the cargo protein.

In one example, the cargo moiety is a toxin. Toxins that are cytotoxic may be herein referred to as "cytotoxins." Exemplary toxins that can be used include pore-forming toxins, and toxins that upon internalization inhibit cell growth. In other examples, cargo moieties are proteins that are apoptotic triggering proteins, and cell growth inhibiting proteins. In some examples, the toxin is a modified bacterial toxin such that the resulting toxin is less immunogenic than the native toxin. Such modified toxins, such as a modified *Pseudomonas* exotoxin A, can reduce the patient's immunogenic response, thereby allowing repeated administration.

Pore forming toxins are toxins that form pores in the cell membrane thereby killing the cell via cell lyses. Exemplary pore forming toxins include but are not limited to human toxins such as perforin or bacterial toxins such as aerolysin as well as modified pore-forming protein toxins that are derived from naturally occurring pore-forming protein toxins (nPPTs) such as aerolysin or aerolysin-related polypeptides. Suitable aerolysin-related nPPTs have the following features: a pore-forming activity that is activated by removal of an inhibitory domain via protease cleavage, and the ability to bind to receptors that are present on cell membranes through one or more binding domains. In some examples the linker can be engineered to be sensitive to a protease or be chemically liable. Additional examples of pore forming toxins that can be used as cargo moieties include, but are not limited to, proaerolysin from *Aeromonas hydrophila, Aeromonas trota* and *Aeromonas salmonicida*, alpha toxin from *Clostridium septicum*, anthrax protective antigen, *Vibrio cholerae* VCC toxin, epsilon toxin from *Clostridium perfringens*, and *Bacillus thuringiensis* delta toxins. A detailed description of the engineering of proaerolysin can be found in U.S. Pat. No. 7,282,476, which is herein incorporated by reference.

Additional toxins that can be used as cargo moieties include toxins that act within a cell. For example, anthrax, diphtheria, cholera, and botulinum toxins include a portion that acts in the cytoplasm, as well as a portion that acts to bind to the cell surface. These toxins, or portions thereof, can be linked to a targeting moiety and used to inhibit cancer cancer cell growth. Select members of the ribonuclease A (RNase A) superfamily are potent cytotoxins. These cytotoxic ribonucleases enter the cytosol, where they degrade cellular RNA and cause cell death.

In some examples ribosome inactivating proteins can be used as toxins. In these examples the cargo moiety is a polypeptide having ribosome-inactivating activity including, without limitation, gelonin, bouganin, saporin, ricin, ricin A chain, bryodin, restrictocin, and variants thereof. Diphtheria toxin and *Pseudomonas* exotoxin A inhibit protein synthesis via ADP-ribosylation of elongation factor 2. When the cargo moiety is a ribosome-inactivating protein or inhibits protein synthesis via ADP-ribosylation of elongation factor 2, the targeted cargo protein can be internalized upon binding to the cancer cell.

Cargo moieties that induce apoptosis can also be used to target cancer cells. Examples of cargo moieties that induce apoptosis include caspases, granzymes and BCL-2 pro-apoptotic related proteins such as BAX (e.g., Accession no: CAE52910), BAD (e.g., Accession no: CAG46757), BAT (e.g., Accession no: AAI07425), BAK (e.g., Accession no: AAA74466), BIK (e.g., Accession no: CAG30276), BOK (e.g., Accession no: AAH06203), BID (e.g., Accession no: CAG28531), BIM (e.g., Accession no: NP_619527) and BMF (e.g., Accession no: AAH69328). These cargo moieties can be used alone or in combination to reduce or inhibit cancer cell growth.

Aerolysin is a channel-forming toxin produced as an inactive protoxin called proaerolysin (PA). Exemplary aerolysin and PA sequences that can be used in a targeted cargo protein are provided in Table 2. The PA protein contains many discrete functionalities that include a binding domain, a toxin domain, and a C-terminal inhibitory peptide domain that contains a protease activation site. The binding domain recognizes and binds to glycophosphatidylinositol (GPI) membrane anchors, such as are found in Thy-1 on T lymphocytes, the PIGA gene product found in erythrocyte membranes and Prostate Stem Cell Antigen (PSCA). The activation or proteolysis site within proaerolysin is a six amino acid sequence that is recognized as a proteolytic substrate by the furin family of proteases. PA is activated upon hydrolysis of a C-terminal inhibitory segment by furin. Activated aerolysin binds to GPI-anchored proteins in the cell membrane and forms a heptamer that inserts into the membrane producing well-defined channels of ~17 Å. Channel formation leads to rapid cell death. Wild-type aerolysin is toxic to mammalian cells, including erythrocytes, for example at 1 nanomolar or less.

In some examples, a target cargo protein is a PA molecule with the native furin site replaced with a different cleavage site, such as prostate-specific protease cleavage site (e.g., a PSA-specific cleavage site, which permits activation of the variant PA in the presence of a prostate-specific protease such as PSA, PMSA, or HK2). In one example, a prostate-specific protease cleavage site is inserted into the native furin cleavage site of PA, such that PA is activated in the presence of a prostate-specific protease, but not furin. In another example, a variant PA molecule further includes a functionally deleted binding domain (e.g., about amino acids 1-83 of a native PA protein sequence). Functional deletions can be made using any method known in the art, such as deletions, insertions, mutations, or substitutions. In some examples, targeted cargo proteins include variant PA molecules in which the native binding domain is functionally deleted and replaced with a prostate-tissue or other tissue-specific binding domain. In other examples, variant PA molecules include a furin cleavage site and a functionally deleted binding domain which is replaced with a prostate-tissue specific binding domain. Such variant PA molecules are targeted to prostate cells via the prostate-tissue specific binding domain, and activated in the presence of furin.

Bouganin is a ribosome-binding protein originally isolated from *Bougainvillea speotabilis* (see U.S. Pat. No. 6,680,296). Exemplary modified bouganins are described in WO 2005/090579 and U.S. Pat. No. 7,339,031. Bouganin damages ribosomes and leads to a cessation of protein synthesis and cell death. Exemplary bouganin proteins that can be used in the targeted cargo proteins of the present disclosure include those in GenBank Accession No. AAL35962, as well as those native and modified bouganin sequences provided in U.S. Pat. Nos. 6,680,296; 7,339,031 and PCT publication WO 2005/090579 (bouganin sequences herein incorporated by reference), as well as sequences having at least 60% sequence identity, at least 75%, at least 80%, at least 85%, at least 90%, at least 95%, at least 98% or even at least 99% sequence identity to such sequences.

BAD, BCL2-associated agonist of cell death, is a regulator of programmed cell death (apoptosis). BAD positively regulates cell apoptosis by forming heterodimers with BCL-xL and BCL-2, and reversing their death repressor activity. Proapoptotic activity of BAD is regulated through its phosphorylation. Exemplary BAD proteins that can be used in the targeted cargo proteins of the present disclosure include those in GenBank Accession Nos. CAG46757; AAH01901.1; and CAG46733.1, as well as those sequences provided in U.S. Pat. No. 6,737,511 (sequences herein incorporated by reference), as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native BAD protein.

BAX, BCL2-associated X protein, is a regulator of programmed cell death (apoptosis). This protein forms a heterodimer with BCL2, and functions as an apoptotic activator. BAX interacts with, and increases the opening of, the mitochondrial voltage-dependent anion channel (VDAC), which leads to the loss in membrane potential and the release of cytochrome c. Exemplary BAX proteins that can be used in the targeted cargo proteins of the present disclosure include those provided by GenBank Accession Nos. CAE52909.1; AAO22992.1; EAW52418.1, U.S. Pat. No. 6,645,490 (Bax in the IL2-Bax construct is a Bax-alpha variant that can be used in the present disclosure), as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native BAX protein.

In some examples, the BAX protein of a targeted cargo protein may be modified such that the C-terminal anchor domain has been deleted and replaced with a CaaX sequence. CaaX is a peptide with the sequence Cysteine-a-a-X where "X" is any amino acid and "a" is an aliphatic amino acid. Because membrane association of BAX is needed for optimal apoptosis activity, addition of membrane binding domains such as CaaX can enhance their proapoptotic activities. Proteins with CaaX sequence are farnesylated. Farnesylated proteins are targeted to membranes (e.g., see Wright and Philip, *J. Lipid Res.,* 2006, 47(5): 883-91). Potential BAX variants containing a CaaX sequence may or may not contain the C-terminal anchor domain.

*Pseudomonas* exotoxin (PE) is a toxin secreted by *Pseudomonas*. Native PE is cytotoxic for mammalian cells due to its ability to enter cells by receptor-mediated endocytosis and then, after a series of intracellular processing steps, translocate to the cell cytosol and ADP-ribosylate elongation factor 2. This results in the inhibition of protein synthesis and cell death. PE has three functional domains: an amino-terminal receptor-binding domain, a middle translocation domain, and a carboxyl-terminal ADP-ribosylation domain. Modified PE molecules can include elimination of domain Ia, as well as deletions in domains II and III. Exemplary PE proteins that can be used in the targeted cargo proteins of the present disclosure include those provided in Table 1, as well as sequences having at least 60% sequence identity, at least 75%, at least 80%, at least 85%, at least 90%, at least 95%, at least 98% or even at least 99% sequence identity to such sequences as long as the variant retains or has enhanced biological activity of the native PE protein.

Thapsigargin is an inhibitor of sarco/endoplasmic reticulum Ca2+ATPases. Thapsigargin is classified as a sesquiterpene lactone, and raises cytosolic calcium concentration by blocking the ability of the cell to pump calcium into the sarcoplasmic and endoplasmic reticulum which causes these stores to become depleted. Store-depletion can secondarily activate plasma membrane calcium channels, allowing an influx of calcium into the cytosol.

Ribonuclease A (RNAseA) is an endonuclease that cleaves single-stranded RNA. RNAse A toxins can be obtained from mammals and reptiles. Exemplary RNAse A proteins that can be used in the targeted cargo proteins of the present disclosure include those provided in Table 2, as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native RNAseA toxin.

The cargo moiety used can include native sequences (such as the GenBank Accession Nos. and sequences present in the patents referenced in Table 2 and listed above), as well as variants thereof, such as a variant having at least 98%, at least 95%, at least 90%, at least 80%, at least 70%, or at least 60% sequence identity with the native cargo moiety, as long as the variant retains or has enhanced biological activity of the native cargo moiety (e.g., at least about this amount of sequence identity to the GenBank Accession Nos. listed in Table 2 and listed above). In some examples, variant sequences retain substantially the same amount (or even more) of the native biological function of the cargo moiety, such as the ability to kill or inhibit the growth of a target cell. A cargo moiety can also be a fragment of the native sequence that retains a substantial amount of the native biological function of the protein.

The cargo moieties are engineered to target cells by linking them to targeting moieties. Targeting moieties include agents that can bind to cell surface molecules or targets.

Making Targeted Cargo Proteins

Targeted cargo proteins can be prepared by many routine methods as known in the art. Targeted cargo proteins, as well as modifications thereto, can be made, for example, by engineering the nucleic acid encoding the targeted cargo protein using recombinant DNA technology or by peptide synthesis. Modifications to the targeted cargo protein may be made, for example, by modifying the targeted cargo protein polypeptide itself, using chemical modifications and/or limited proteolysis. Combinations of these methods may also be used to prepare the targeted cargo proteins.

Methods of cloning and expressing proteins are well-known in the art, detailed descriptions of techniques and systems for the expression of recombinant proteins can be found, for example, in Current Protocols in Protein Science (Coligan, J. E., et al., Wiley & Sons, New York). Those skilled in the art will understand that a wide variety of expression systems can be used to provide the recombinant protein. Accordingly, the targeted cargo proteins can be produced in a prokaryotic host (e.g., *E. coli, A. salmonicida* or *B. subtilis*) or in a eukaryotic host (e.g., *Saccharomyces* or *Pichia*; mammalian cells, e.g., COS, NIH 3T3, CHO, BHK, 293, or HeLa cells; or insect cells). The targeted cargo proteins can be purified from the host cells by standard techniques known in the art.

Sequences for various exemplary targeting moieties and cargo moieties are provided in the Tables 1 and 2. Variants and homologs of these sequences can be cloned, if an alternative sequence is desired, using standard techniques [see, for example, Ausubel et al., Current Protocols in Molecular Biology, Wiley & Sons, NY (1997 and updates); Sambrook et al., supra]. For example, the nucleic acid sequence can be obtained directly from a suitable organism, such as *Aeromonas hydrophila*, by extracting mRNA and then synthesizing cDNA from the mRNA template (for example by RT-PCR) or by PCR-amplifying the gene from genomic DNA. Alternatively, the nucleic acid sequence encoding either the targeting moiety or the cargo moiety can be obtained from an appropriate cDNA library by standard procedures. The isolated cDNA is then inserted into a suitable vector, such as a cloning vector or an expression vector.

Mutations (if desired) can be introduced at specific, pre-selected locations by in vitro site-directed mutagenesis techniques well-known in the art. Mutations can be introduced by deletion, insertion, substitution, inversion, or a combination thereof, of one or more of the appropriate nucleotides making up the coding sequence.

The expression vector can further include regulatory elements, such as transcriptional elements, required for efficient transcription of the targeted cargo protein-encoding sequences. Examples of regulatory elements that can be incorporated into the vector include, but are not limited to, promoters, enhancers, terminators, and polyadenylation signals. Vectors that include a regulatory element operatively linked to a nucleic acid sequence encoding a genetically engineered targeted cargo protein can be used to produce the targeted cargo protein.

The expression vector may additionally contain heterologous nucleic acid sequences that facilitate the purification of the expressed targeted cargo protein, such as affinity tags such (e.g., metal-affinity tags, histidine tags, avidin/streptavidin encoding sequences, glutathione-S-transferase (GST) encoding sequences, and biotin encoding sequences). In one example, such tags are attached to the N- or C-terminus of a targeted cargo protein, or can be located within the targeted cargo protein. The tags can be removed from the expressed targeted cargo protein prior to use according to methods known in the art. Alternatively, the tags can be retained on the targeted cargo protein, providing that they do not interfere with the ability of the targeted cargo protein to target and kill (or decrease growth of) cancer cells.

As an alternative to a directed approach to introducing mutations into naturally occurring pore-forming proteins, a cloned gene expressing a pore-forming protein can be subjected to random mutagenesis by techniques known in the art. Subsequent expression and screening of the mutant forms of the protein thus generated would allow the identification and isolation of targeted cargo moieties.

The targeted cargo proteins can also be prepared as fragments or fusion proteins. A fusion protein is one which includes a targeted cargo protein linked to other amino acid sequences that do not inhibit the ability of the targeted cargo protein to selectively target and inhibit cancer cell growth or kill cancer cells. In an alternative example, the other amino acid sequences are short sequences of, for example, up to about 5, about 6, about 7, about 8, about 9, about 10, about 20, about 30, about 50 or about 100 amino acid residues in length. These short sequences can be linker sequences as described above.

Methods for making fusion proteins are well known to those skilled in the art. For example U.S. Pat. No. 6,057,133 discloses methods for making fusion molecules composed of human interleukin-3 (hIL-3) variant or mutant proteins functionally joined to a second colony stimulating factor, cytokine, lymphokine, interleukin, hematopoietic growth factor or IL-3 variant. U.S. Pat. No. 6,072,041 to Davis et al. discloses the generation of fusion proteins comprising a single chain Fv molecule directed against a transcytotic receptor covalently linked to a therapeutic protein.

The targeted cargo protein can include one or more linkers, as well as other moieties, as desired. These can include a binding region, such as avidin or an epitope, or a tag such as a polyhistidine tag, which can be useful for purification and processing of the fusion protein. In addition, detectable markers can be attached to the fusion protein, so that the traffic of the fusion protein through a body or cell can be monitored conveniently. Such markers include radionuclides, enzymes, fluorophores, chromophores, and the like.

One of ordinary skill in the art will appreciate that the DNA can be altered in numerous ways without affecting the biological activity of the encoded protein. For example, PCR can be used to produce variations in the DNA sequence which encodes a targeted cargo protein. Such variations in the DNA sequence encoding a targeted cargo protein can be used to optimize for codon preference in a host cell used to express the protein, or may contain other sequence changes that facilitate expression.

A covalent linkage of a targeting moiety directly to a cargo moiety or via a linker may take various forms as is known in the art. For example, the covalent linkage may be in the form of a disulfide bond. The DNA encoding one of the components can be engineered to contain a unique cysteine codon. The second component can be derivatized with a sulfhydryl group reactive with the cysteine of the first component. Alternatively, a sulfhydryl group, either by itself or as part of a cysteine residue, can be introduced using solid phase polypeptide techniques. For example, the introduction of sulfhydryl groups into peptides is described by Hiskey (*Peptides* 3:137, 1981).

Proteins also can be chemically modified by standard techniques to add a sulfhydryl group. For example, Traut's reagent (2-iminothiolane-HCl) (Pierce Chemicals, Rockford, Ill.) can be used to introduce a sulfhydryl group on primary amines, such as lysine residues or N-terminal amines. A protein or peptide modified with Traut's reagent can then react with a protein or peptide which has been modified with reagents such as N-succinimidyl 3-(2-pyridyldithio) propionate (SPDP) or succinimidyl 4-(N-maleimidomethyl)cyclohexane-1-carboxylate (SMCC) (Pierce Chemicals, Rockford, Ill.).

The components can also be joined using the polymer, monomethoxy-polyethylene glycol (mPEG), as described in Maiti et al., *Int. J. Cancer* Suppl., 3:17-22, 1988.

The targeting moiety and the cargo moiety can also be conjugated through the use of standard conjugation chemistries as is known in the art, such as carbodiimide-mediated coupling (for example, DCC, EDC or activated EDC), and the use of 2-iminothiolane to convert epsilon amino groups to thiols for crosslinking and m-maleimidobenzoyl-n-hydroxysuccinimidyl ester (MBS) as a crosslinking agent.

Linking of a cargo moiety to a targeting moiety may be direct meaning that one portion of the cargo moiety is directly attached to a portion of the targeting moiety. For example, one end of the amino acid sequence of a cargo protein can be directly attached to an end of the amino acid sequence of the targeting moiety. For example, the C-terminus of the cargo protein can be linked to the N-terminus of the targeting moiety, or the C-terminus of the targeting moiety can be linked to the N-terminus of the cargo protein. Methods of generating such fusion proteins are routine in the art, for example using recombinant molecular biology methods.

In another example, the cargo moiety is linked to the targeting moiety indirectly through a linker. The linker can serve, for example, simply as a convenient way to link the two entities, as a means to spatially separate the two entities, to provide an additional functionality to the targeted cargo protein, or a combination thereof.

In general, the linker joining the targeting moiety and the cargo moiety can be designed to (1) allow the two molecules to fold and act independently of each other, (2) not have a propensity for developing an ordered secondary structure which could interfere with the functional domains of the two moieties, (3) have minimal hydrophobic or charged characteristic which could interact with the functional protein domains and/or (4) provide steric separation of the two regions. For example in some instances it may be desirable to spatially separate the targeting moiety and the cargo moiety to prevent the targeting moiety from interfering with the inhibitory activity of the targeted cargo moiety and/or the cargo moiety interfering with the targeting activity of the targeting moiety. The linker can also be used to provide, for example, lability to the connection between the targeting moiety and the cargo moiety, an enzyme cleavage site (for example a cleavage site for a protease), a stability sequence, a molecular tag, a detectable label, or various combinations thereof.

The linker can be bifunctional or polyfunctional, e.g. contains at least about a first reactive functionality at, or proximal to, a first end of the linker that is capable of bonding to, or being modified to bond to, the targeting moiety and a second reactive functionality at, or proximal to, the opposite end of the linker that is capable of bonding to, or being modified to bond to, the cargo moiety being modified. The two or more reactive functionalities can be the same (i.e. the linker is homobifunctional) or they can be different (i.e. the linker is heterobifunctional). A variety of bifunctional or polyfunctional cross-linking agents are known in the art that are suitable for use as linkers (for example, those commercially available from Pierce Chemical Co., Rockford, Ill.), such as avidin and biotin. Alternatively, these reagents can be used to add the linker to the targeting moiety and/or cargo moiety.

The length and composition of the linker can be varied considerably provided that it can fulfill its purpose as a molecular bridge. The length and composition of the linker are generally selected taking into consideration the intended function of the linker, and optionally other factors such as ease of synthesis, stability, resistance to certain chemical and/or temperature parameters, and biocompatibility. For example, the linker should not significantly interfere with the ability of the targeting moiety to target the targeted cargo protein to a cancer cell, or with the activity of the targeted cargo protein relating to activation, pore-forming ability, or toxin activity.

Linkers suitable for use may be branched, unbranched, saturated, or unsaturated hydrocarbon chains, as well as peptides as noted above. Furthermore, if the linker is a peptide, the linker can be attached to the targeting moiety and/or the cargo moiety using recombinant DNA technology. Such methods are well-known in the art and details of this technology can be found, for example, in Sambrook et al., supra.

In one example, the linker is a branched or unbranched, saturated or unsaturated, hydrocarbon chain having from 1 to 100 carbon atoms, wherein one or more of the carbon atoms is optionally replaced by —O— or —NR— (wherein R is H, or C1 to C6 alkyl), and wherein the chain is optionally substituted on carbon with one or more substituents selected from the group of (C1-C6) alkoxy, (C3-C6) cycloalkyl, (C1-C6) alkanoyl, (C1-C6) alkanoyloxy, (C1-C6) alkoxycarbonyl, (C1-C6) alkylthio, amide, azido, cyano, nitro, halo, hydroxy, oxo (=O), carboxy, aryl, aryloxy, heteroaryl, and heteroaryloxy.

Examples of suitable linkers include, but are not limited to, peptides having a chain length of 1 to 500 amino acid residues (such as 1 to 100, 1 to 50, 6 to 30, such as less than 30 amino acids). Typically surface amino acids in flexible protein regions include Gly, Asn and Ser. Other neutral amino acids, such as Thr and Ala, can also be used in the linker sequence. Additional amino acids can be included in the linker to provide unique restriction sites in the linker sequence to facilitate construction of the fusions. Other exemplary linkers include those derived from groups such as ethanolamine, ethylene glycol, polyethylene with a chain length of 6 to 100 carbon atoms, polyethylene glycol with 3 to 30 repeating units, phenoxyethanol, propanolamide, butylene glycol, butyleneglycolamide, propyl phenyl, and ethyl, propyl, hexyl, steryl, cetyl, and palmitoyl alkyl chains.

In one example, the linker is a branched or unbranched, saturated or unsaturated, hydrocarbon chain, having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (=O), carboxy, aryl and aryloxy.

In a specific example, the linker is a peptide having a chain length of 1 to 50 amino acid residues, such as 1 to 40, 1 to 20, or 5 to 10 amino acid residues.

Peptide linkers that are susceptible to cleavage by enzymes of the complement system, urokinase, tissue plasminogen activator, trypsin, plasmin, or another enzyme having proteolytic activity may be used in one example. According to another example, the targeted cargo protein includes a targeting moiety attached via a linker susceptible to cleavage by enzymes having a proteolytic activity such as a urokinase, a tissue plasminogen activator, plasmin, thrombin or trypsin. In addition, targeting moieties may be attached to the cargo moiety via disulfide bonds (for example, the disulfide bonds on a cysteine molecule). Since many tumors naturally release high levels of glutathione (a reducing agent) this can reduce the disulfide bonds with subsequent release of the cargo moiety at the site of delivery.

In one example, the targeted cargo protein includes a targeting moiety linked by a cleavable linker region. In another example, the cleavable linker region is a protease-cleavable linker, although other linkers, cleavable for example by small molecules, may be used. Examples of protease cleavage sites are those cleaved by factor Xa, thrombin and collagenase. In one example, the protease cleavage site is one that is cleaved by a protease that is associated with a disease. In another example, the protease cleavage site is one that is cleaved by a protease that is up-regulated or associated with cancers in general.

Examples of such proteases are uPA, the matrix metalloproteinase (MMP) family, the caspases, elastase, prostate specific antigen (PSA, a serine protease), and the plasminogen activator family, as well as fibroblast activation protein. In still another example, the cleavage site is cleaved by a protease secreted by cancer-associated cells. Examples of these proteases include matrixmetalloproteases, elastase, plasmin, thrombin, and uPA. In another example, the protease cleavage site is one that is up-regulated or associated with a specific cancer. The precise sequences are available in the art and the skilled person will have no difficulty in selecting a suitable cleavage site. By way of example, the protease cleavage region targeted by Factor Xa is I E G R. The protease cleavage region targeted by enterokinase is D D D D K. The protease cleavage region targeted by thrombin is L V P R G. In one example, the cleavable linker region is one which is targeted by endocellular proteases.

As known in the art, the attachment of a linker to cargo moiety (or of a linker element to a cleavable element, or a cleavable element to another cargo moiety) need not be a particular mode of attachment or reaction.

Testing Targeted Cargo Proteins

Targeted cargo proteins can be tested using standard techniques known in the art. Exemplary methods of testing candidate targeted cargo proteins are provided below and in the examples included herein. One of ordinary skill in the art will understand that other methods of testing the targeted cargo proteins are known in the art and are also suitable for testing candidate targeted cargo proteins. For example, methods known in the art for testing for anti-tumor activity can be used. The targeted cargo proteins can initially be screened against a panel of tumor cell lines. A cell proliferation assay, such as the WST-1 kit sold by Roche, can be used. Potency can be evaluated using different drug concentrations in the presence or absence of active agents that inhibit cancer cells. Selected drug candidates from the initial tumor cell screen can be further characterized through additional in vitro assays and in relevant xenograft models to examine anti-tumor activity, such as those described in the Examples herein.

Use of Targeted Cargo Proteins in Combination with Active Agents

Targeted cargo proteins of the invention may be administered by parenteral means, including subcutaneous, intravenous or intramuscular injection, or by injection into a body cavity. Parenteral administration by intravenous injection or infusion is preferred. Alternatively, targeted cargo proteins may be administered by direct injection or infusion into a tumor, for example a brain tumor or a prostate tumor. Alternative methods of administration of the targeted cargo proteins will be evident to one of ordinary skill in the art. Such methods may include for example, the use of catheters or implantable pumps to provide continuous infusion over a period of several hours to several days into the subject in need of treatment. It is anticipated that active agents will be administered by the routes that are currently in use for their administration in clinical settings.

The dosages of targeted cargo proteins to be administered to a subject are not subject to absolute limits, but will depend on the nature of the targeted cargo protein and its unwanted side effects, the subject being treated and the type of condition being treated and the manner of administration. Generally the dose will be a therapeutically effective amount. (A therapeutically effective amount of a targeted cargo protein can be determined in various ways, such as assaying for improvement of the condition of a subject having cancer by monitoring the size of a tumor in a subject, the partial or complete alleviation of symptoms, halting the growth of a tumor, or decreasing the size of a tumor. Effective amounts may also be determined through various in vitro or in vivo assays similar to the ones described in the Examples provided herein.)

The therapeutically effective dose will also depend on whether administration is parenteral or local. For parenteral administration of targeted cargo proteins, exemplary dosages for administration to a subject for a single treatment may range from 10 ng to 10 mg per square meter ($m^2$) of body surface area, from 1 µg to 1 mg per $m^2$ of body surface area, and from 10 µg to 100 µg per square meter ($m^2$) of body surface area. For localized treatment (such as injection or infusion into a brain tumor) a single treatment may comprise a dosage of targeted cargo protein ranging from 10 ng to 10 mg, from 10 µg to about 1 mg, or from 25 µg to 0.5 mg.

Treatments with targeted cargo proteins may be completed in a single day, or may be done repeatedly on multiple days with the same or a different dosage. Repeated treatments may be done on the same day, on successive days, or every 1-3 days, every 3-7 days, every 1-2 weeks, every 2-4 weeks, every 1-2 months, or at even longer intervals.

Dosages of the active agents are determined in accordance with current clinical protocols for the active agent being used.

It is anticipated that the therapeutic dosages of either the targeted cargo proteins or the active agents when used in combination may be reduced from what would otherwise be determined to be the optimal level for each agent administered alone due to the synergy between the targeted cargo protein and the active agent.

The active agents may be administered concurrently with the targeted cargo proteins, or within hours or days. In some embodiments, the active agent is administered within 24, 48, 72 or 96 hours of administration of the targeted cargo protein. The active agents may be administered more or less frequently than the targeted cargo proteins. For example, when repeat treatments with a targeted cargo protein are given, some treatments, but not others, may be done in conjunction with an active agent. Treatment with the active agent may be done more of less frequently than treatment with the targeted cargo protein.

Pharmaceutical Compositions

Pharmaceutical compositions can include one or more targeted cargo proteins and/or one or more active agents, and one or more non-toxic pharmaceutically acceptable carriers, diluents, excipients and/or adjuvants. If desired, other active ingredients may be included in the compositions. As indicated above, such compositions are suitable for use in the treatment of cancer. The term "pharmaceutically acceptable carrier" refers to a carrier medium which does not interfere with the effectiveness of the biological activity of the active ingredients and which is not toxic to the host or patient. Representative examples are provided below.

The pharmaceutical compositions may comprise, for example, from about 1% to about 95% of a targeted cargo protein. Compositions formulated for administration in a single dose form may comprise, for example, about 20% to about 90% of the targeted cargo proteins, whereas compositions that are not in a single dose form may comprise, for example, from about 5% to about 20% of the targeted cargo proteins. Concentration of the targeted cargo protein in the final formulation can be at least 1 ng/mL, such as at least 1 µg/mL or at least 1 mg/mL. For example, the concentration in the final formulation can be between about 0.01 µg/mL and about 1,000 µg/mL. In one example, the concentration in the final formulation is between about 0.01 mg/mL and about 100 mg/mL.

The targeted cargo proteins can be delivered along with a pharmaceutically acceptable vehicle. In one example, the vehicle may enhance the stability and/or delivery properties. Thus, the disclosure also provides for formulation of the targeted cargo protein with a suitable vehicle, such as an artificial membrane vesicle (including a liposome, noisome, nanosome and the like), microparticle or microcapsule, or as a colloidal formulation that comprises a pharmaceutically acceptable polymer. The use of such vehicles/polymers may be beneficial in achieving sustained release of the targeted cargo proteins. Alternatively, or in addition, the targeted cargo protein formulations can include additives to stabilize the protein in vivo, such as human serum albumin, or other stabilizers for protein therapeutics known in the art. Targeted cargo protein formulations can also include one or more viscosity enhancing agents which act to prevent backflow of the formulation when it is administered, for example by injection or via catheter. Such viscosity enhancing agents include, but are not limited to, biocompatible glycols and sucrose.

Pharmaceutical compositions formulated as aqueous suspensions contain the active compound(s) in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-β-cyclodextrin, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, or one or more coloring agents.

Compositions can be preserved by the addition of an anti-oxidant such as ascorbic acid.

The pharmaceutical compositions can be formulated as a dispersible powder or granules, which can subsequently be used to prepare an aqueous suspension by the addition of water. Such dispersible powders or granules provide the active ingredient in admixture with one or more dispersing or wetting agents, suspending agents and/or preservatives. Suitable dispersing or wetting agents and suspending agents are exemplified by those already mentioned above.

Pharmaceutical compositions can also be formulated as oil-in-water emulsions. The oil phase can be a vegetable oil, for example, olive oil or arachis oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monooleate.

The pharmaceutical compositions containing one or more targeted cargo proteins and/or one or more active agents can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

In one example, the targeted cargo protein is conjugated to a water-soluble polymer, e.g., to increase stability or circulating half life or reduce immunogenicity. Clinically acceptable, water-soluble polymers include, but are not limited to, polyethylene glycol (PEG), polyethylene glycol propionaldehyde, carboxymethylcellulose, dextran, polyvinyl alcohol (PVA), polyvinylpyrrolidone (PVP), polypropylene glycol homopolymers (PPG), polyoxyethylated polyols (POG) (e.g., glycerol) and other polyoxyethylated polyols, polyoxyethylated sorbitol, or polyoxyethylated glucose, and other carbohydrate polymers. Methods for conjugating polypeptides to water-soluble polymers such as PEG are described, e.g., in U.S. patent Pub. No. 20050106148 and references cited therein. In one example the polymer is a pH-sensitive polymers designed to enhance the release of drugs from the acidic endosomal compartment to the cytoplasm (see for example, Henry et al., *Biomacromolecules* 7(8):2407-14, 2006).

Active agents may be included in a pharmaceutical formulation together with target cargo proteins for co-administration, or may be formulated separately. They may be formulated in conventional pharmaceutically acceptable carriers. (vehicles) such as those found in Remington's Pharmaceutical Sciences, by E. W. Martin, Mack Publishing Co., Easton, Pa., 15th Edition (1975), describes compositions and formulations suitable for pharmaceutical delivery of active agents or the targeted cargo protein molecules provided herein.

Diseases or Conditions that May be Treated by the Methods of the Disclosure

Diseases or conditions that may be treated using the methods of the disclosure are characterized by cells that uniquely express, or over-express, at least one target molecule that specifically binds to a targeted cargo protein. Such diseases or conditions may include various inflammatory conditions as well as benign tumors or malignant tumors (cancer). Tumors can be solid or hematological. Examples of hematological tumors include, but are not limited to: leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelogenous leukemia, and chronic lymphocytic leukemia), myelodysplastic syndrome, and myelodysplasia, polycythemia vera, lymphoma, (such as Hodgkin's disease, all forms of non-Hodgkin's lymphoma), multiple myeloma, Waldenstrom's macroglobulinemia, and heavy chain disease.

Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, lung cancer, ovarian cancer, prostate cancer, benign prostatic hyperplasia, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, epithelial tumors (e.g., cervical cancer, gastric cancer, skin cancer, head and neck tumors), testicular tumor, bladder carcinoma, melanoma, brain tumors, and CNS tumors (such as a glioma, astrocytoma, medulloblastoma, craniopharyogioma, ependymoma, pinealoma, hemangioblastoma, acoustic neuroma, oligodendroglioma, menangioma, meningioma, neuroblastoma and retinoblastoma).

Preferred diseases and conditions that may be treated by the methods of the invention include brain cancer, including malignant astrocytoma and gliobastoma multiforme, Kaposi sarcoma, bladder cancer, renal cell cancer, breast cancer, pancreatic cancer, non-small cell lung cancer, thyroid cancer, squamous cell carcinoma of the head and neck, colon cancer and other cancers of the gastrointestinal system, mesothelioma and prostate cancer.

EXAMPLES

Example 1

We have observed that 42 of 70 (60%) tumor samples from patients with PDA express moderate- to high-density surface IL-4 receptor (IL-4R), whereas normal pancreatic samples express no or low-density IL-4R. PRX321 was specifically and highly cytotoxic [50% protein synthesis inhibition (IC50) ranging from >0.1 to 13 ng/mL] to six of eight pancreatic cancer cell lines, whereas no cytotoxicity (IC50>1,000 ng/mL) was observed in normal human pancreatic duct epithelium cells, fibroblasts, and human umbilical vein endothelial cells (HUVEC). We also showed that PRX321 in combination with gemcitabine exhibited synergistic antitumor activity in vitro. To confirm synergistic antitumor activity in vivo and monitor precise real-time disease progression, we used a novel metastatic and orthotopic mouse model using green fluorescent protein—transfected cancer cells and whole-body imaging system. The combination of both agents caused complete eradication of tumors in 40% of nude mice with small established PDA tumors. In addition, combined treatment significantly prolonged the survival of nude mice bearing day 14 advanced distant metastatic PDA tumors. Similar results were observed in mice xenografted with PDA obtained from a patient undergoing surgical resection. These results indicate that PRX321 combined with gemcitabine may provide effective therapy for the treatment of patients with PDA.

Example 2

In this study, we examined expression of IL-4R in samples derived from PDA and the efficacy of PRX321, gemcitabine, and combination of both in primary and metastatic tumor models. To imitate aggressive clinical situation and to monitor precise real-time disease progression, we used a novel metastatic and orthotopic advanced pancreatic cancer model using retroviral green fluorescent protein (GFP)-transfected pancreatic cancer cell line and whole-body imaging system (27). Together, our study shows that PRX321 synergizes with gemcitabine, significantly inhibiting the growth of primary and metastatic tumor lesions, prolonging the survival time, and completely eradicating tumors in 40% of mice in an early pancreatic cancer model.

Example 3

Materials and Methods

Cell culture, reagents, and tissue specimens. Cell lines were obtained from the American Type Culture Collection and Sciencell. Human pancreatic duct epithelium (HPDE) cells were cultured routinely in keratinocyte serum-free medium supplemented with bovine pituitary extract and epidermal growth factor (Life Technologies; ref. 28). PRX321 [IL4(38-37)-PE38KDEL] was produced as described previously (23). Fifteen paraffin-embedded tissue sections and tissue arrays containing 70 tumor specimens were obtained from Cooperative Human Tissue Network and U.S. Biomax, respectively. Gemcitabine was procured through the pharmacy of the clinical center (NIH).

Immunohistochemistry and flow cytometry. Immunohistochemistry was done as described previously (24). Deparafinized tissue sections were incubated with anti-human IL-4Ra polyclonal antibody (Santa Cruz Biotechnology) or isotype control (IgG). The results were scored on the basis of the density of staining 0%, 0% to 10%, 11% to 50%, 51% to 100% as negative, weak, moderate, and strong, respectively. Tissue sections for IL-4R were evaluated by Dr. Satoru Takahashi who is a pathologist at Nagoya City University in Japan.

Expression of IL-4Ra on pancreatic cancer cell lines and HPDE cells was assessed by flow cytometry using phycoerythrin-conjugated anti-IL-4Ra monoclonal antibody as previously described (29). Staining with isotype Matched IgG served as control. Protein synthesis inhibition assay and assessment of synergism or antagonism. The in vitro cytotoxic activity of PRX321, gemcitabine, and their combination was measured by the inhibition of protein synthesis (18). Drug interaction between PRX321 and gemcitabine was assessed at a concentration ratio of 1:1, using the combination index (CI), where CI<1, CI=1, and CI>1 indicate synergistic, additive, and antagonistic effects, respectively (30). On the basis of the isobologram analysis for mutually exclusive effects, the CI value was calculated as follows:

$$CI = \frac{(D)_1}{(D_x)_1} + \frac{(D)_2}{(D_x)_2}$$

where (Dx)1 and (Dx)2 are the concentrations of PRX321 and gemcitabine, respectively, required to inhibit cell growth by 50%, and (D)1 and (D)2 are the drug concentrations in combination treatments that also inhibit cell growth by 50% (isoeffective compared with the single drugs). Semiquantitative and real-time TaqMan reverse transcription-PCR. Semiquantitative reverse transcription-PCR (RT-PCR) was done as described previously (31). Quantification of IL-4Ra mRNA expression levels in pancreatic cancer cell lines was determined by real-time RT-PCR using a set of IL-4Ra-specific TaqMan probe (5-FAM, 3-MGB) and primers (Applied Biosystems; ref. 24). Gene expression was normalized to glyceraldehyde-3-phosphate dehydrogenase or h-actin before the fold change in gene expression was calculated.

Retroviral transduction and selection of high-GFP-expressing MIAPaCa-2 pancreatic cancer cells. MIA-PaCa-2 cells expressing GFP were established using a 1:1 precipitated mixture of retroviral supernatants of the HEK293 cells and RPMI 1640 (Life Technologies, Inc.), as described previously (32).

Animals. Severe combined immunodeficient (SCID) mice and nude nu/nu mice between age 5 and 6 weeks were maintained in a barrier facility on HEPA-filtered racks. All animal studies were conducted under an approved protocol in accordance with the principles and procedures outlined in the NIH Guideline for the Care and Use of Laboratory Animals.

Whole-body imaging. The tumor-bearing mice were periodically examined in a fluorescence light box illuminated by fiberoptic light at 440/20 nm wavelength (Lightools Research, Inc.). Emitted fluorescence was collected through a long-pass filter GG475 (Chroma Technology) on a Hamamatsu C5810 3-chip cooled color charge coupled device camera (Hamamatsu Photonics Systems). Real-time determination of tumor burden was done by quantifying fluorescent surface area as described previously (32).

Surgical orthotopic implantation of MIA-PaCa-2-GFP tumors. MIA-PaCa-2-GFP cells were injected s.c. into the right dorsal flank of nude mice. Pancreatic tumors, grown s.c. in nude mice, were cut with scissors and minced into f3% 3% 3-mm pieces. For orthotopic surgery, the pancreas was carefully exposed, and tumor chunks were transplanted on the middle of the pancreas with a 6-0 Dexon surgical suture (Davis-Geck, Inc.). The pancreas was then returned to the peritoneal cavity, the abdominal wall, and the skin was closed with 6-0 Dexon sutures.

Experimental design and treatment. For early pancreatic cancer model, primary tumor lesions were detected by external whole-body imaging on day 4 after transplantation. Once the tumors were visualized, mice were randomized into four groups of 10 each. Treatment was initiated on day 5. For advanced pancreatic cancer model, primary and metastasis tumor lesions were detected by external whole-body imaging on day 14 post-transplantation of tumor chunk and randomized into four groups of 10 mice each. Treatment was initiated on day 15.

Primary and orthotopic pancreatic cancer model using a clinical sample. Primary pancreatic cancer specimens were obtained from a patient undergoing radical pancreatectomy at National Cancer Institute under institutional review board-approved protocol. Viable tumor tissue from specimen was cut into small pieces (3% 3% 3 mm) and implanted in the pancreas of 5- to 6-week-old male SCID mice. Primary xenografts were propagated continuously in SCID mice for in vivo testing. Clinical sample-bearing mice were also treated after day 31 by the same protocol as described above.

Statistical analysis. The mean tumor volume in therapeutic and control groups was analyzed by ANOVA. Survival curves were generated by Kaplan-Meier method and compared by using the log-rank test.

Results

Expression of IL-4R in PDA Tissues.

Tissue sections from 15 normal pancreas and 70 PDA specimens were analyzed by immunohistochemical analysis for the expression of IL-4Ra (data not shown). Tumor specimens showed weak to strong staining for IL-4Ra in PDAs. Only weak staining was observed in tumor-infiltrating stromal fibroblasts and endothelial cells. When the proportion of IL-4Ra-positive cancer cells was counted, 23 of 70 primary tumors classified into strong expression group, 19 into moderate expression group, 11 into weak expression group, and 17 into the negative expression group. Thus, 42 of 70 (60%) PDA samples expressed moderate to high density IL-4Ra. In contrast, only 2 of 15 normal pancreas samples showed weak staining for IL-4Ra in normal acinar and ductal cells.

Pancreatic Cancer Cell Lines Expressing IL-4R are Sensitive to PRX321.

We examined the expression of IL-4Ra mRNA by RT-PCR and real-time RT-PCR in eight pancreatic cancer and one normal HPDE cell lines. Six of eight cancer cell lines showed varied density of IL-4Ra mRNA expression, whereas HPAF-II, PK-1, and HPDE cell lines showed no expression (data not shown). Real-time RT-PCR analysis confirmed conventional RT-PCR results and showed that MIA-PaCa-2 and SW1990 cell lines expresses highest level of IL-4Ra mRNA, followed by Capan-1, ASPC-1, Panc-1, and HS766T cell lines. Flow cytometric analysis confirmed mRNA expression data and showed that IL-4Ra is expressed on the cell surface of three pancreatic cancer cell lines but not in normal HPDE cells.

Next, we determined the sensitivity of pancreatic cancer cell lines to PRX321 by protein synthesis inhibition assay, which has been shown to be directly proportional to cell death (19). PRX321 inhibited protein synthesis of pancreatic cancer cell lines in a concentration-dependent manner. MIA-PaCa-2 and SW1990 cell lines were extremely sensitive to the cytotoxin (IC50 0.08 and 0.36 ng/mL, respectively), followed by Capan-1 (IC50 7 ng/mL) and HS766T (IC50 13 ng/mL;). IC50 in Panc-1 and ASPC-1 cell lines was <10 ng/mL. Consistent with the lack of IL-4Ra mRNA expression, HPAF-II and PK-1 cell lines were not sensitive to PRX321 (IC50 z 1,000 ng/mL; data not shown).

The cytotoxic activity of PRX321 was neutralized by incubation with an excess of IL-4, suggesting specific cytotoxicity through binding of PRX321 to IL-4R (data not shown). We also examined the cytotoxicity of PRX321 in fibroblast, HUVEC, and HPDE cell lines, because some of the specimens revealed weak expression of IL-4Ra in non-tumor cells. However, PRX321 was not found to be cytotoxic to these cells (IC50 z 1,000 ng/mL;). The PRX321 cytotoxic activity correlated with extent of IL-4Ra expression. For example, MIAPaCa-2 cells showed lowest IC50 and highest density IL-4R expression as determined by flow cytometric and real-time PCR analyses whereas PK-1 cell line showed highest IC50 as this cell line showed undetectable level of mRNA expression. We also used another cytotoxin IL-13 *Pseudomonas* exotoxin, an IL-13 receptor specific fusion protein (12), to assess the cytotoxicity to pancreatic cancer cell line. However, IL-13 cytotoxin was not cytotoxic to HPAF-II cells (IC50 z1,000 ng/mL).

Synergistic Cytotoxicity of PRX321 and Gemcitabine in Pancreatic Cancer Cell Lines.

Gemcitabine alone mediated a dose-dependent inhibition of protein synthesis with IC50 of 22 nmol/L in MIA-PaCa-2 cells, 3.2 nmol/L in Capan-1 cells, 1,000 nmol/L in SW1990 cells, and 14 nmol/L in HS766T cells (Table 3). When it was combined with PRX321, the protein synthesis inhibition in MIA-PaCa-2 cells was greatly enhanced: IC50 of PRX321 became 0.012, 0.001, and 0.00004 ng/mL by adding 0.03, 0.3, and 3 nmol/L gemcitabine, respectively. These same phenomena were also observed in SW1990 and Capan-1 cells, but not in HS766T cells. The combination index at IC50 and IC75 (concentration of drug causing 75% inhibition of protein synthesis) in MIA-PaCa-2, SW1990, and Capan-1 cells was <1 at all concentrations of gemcitabine (Table 3).

TABLE 3

Cytotoxicity of IL-4 cytotoxin (PRX321), gemcitabine, and their combination in pancreatic cancer cell lines

| Cancer cell line | Drug | IC50* | IC75** |
|---|---|---|---|
| MIA-PaCa-2 | IL-4 cytotoxin | 0.065 ng/mL | 0.32 ng/mL |
| | Gemcitabine | 22 nmol/L | 280 nmol/L |
| Capan-1 | IL-4 cytotoxin | 3.5 ng/mL | 22 ng/mL |
| | Gemcitabine | 3.2 nmol/L | 9 nmol/L |
| SW1990 | IL-4 cytotoxin | 0.36 ng/mL | 1 ng/mL |
| | Gemcitabine | 1,000 nmol/L | 3,000 nmol/L |

| | | CI## | |
|---|---|---|---|
| | | IC50 | IC75 |
| MIA-PaCa-2 | IL-4 cytotoxin + gemcitabine 0.03 nmol/L | 0.153 | 0.563 |
| | IL-4 cytotoxin + gemcitabine 0.3 nmol/L | 0.0336 | 0.094 |
| | IL-4 cytotoxin + gemcitabine 3 nmol/L | 0.137 | 0.0138 |
| Capan-1 | IL-4 cytotoxin + gemcitabine 0.003 nmol/L | 0.287 | 0.34 |
| | IL-4 cytotoxin + gemcitabine 0.03 nmol/L | 0.026 | 0.0713 |
| | IL-4 cytotoxin + gemcitabine 0.3 nmol/L | 0.096 | 0.0603 |
| | IL-4 cytotoxin + gemcitabine 3 nmol/L | 0.938 | 0.401 |
| SW1990 | IL-4 cytotoxin + gemcitabine 0.003 nmol/L | 0.5 | 0.65 |
| | IL-4 cytotoxin + gemcitabine 0.03 nmol/L | 0.27 | 0.5 |
| | IL-4 cytotoxin + gemcitabine 0.3 nmol/L | 0.021 | 0.3 |
| | IL-4 cytotoxin + gemcitabine 3 nmol/L | 0.014 | 0.19 |
| | IL-4 cytotoxin + gemcitabine 30 nmol/L | 0.03 | 0.11 |
| | IL-4 cytotoxin + gemcitabine 300 nmol/L | 0.3 | 0.31 |

NOTE:
CI < 1, CI = 1, and CI > 1 indicate synergistic, additive, and antagonistic effects, respectively.
*Fifty percent protein synthesis inhibition.
**Seventy-five percent protein synthesis inhibition.
CI values were calculated using the formula described in Materials and Methods.

Example 4

In Vivo Whole-Body Optical Imaging of PDA

We developed pancreatic cancer models to investigate antitumor effects of PRX321 and showed its correlation with imaging studies in vivo. Pancreatic cancer cells were transfected with GFP. Our transfection technique using retroviral vector revealed consistent bright GFP fluorescence of MIA-PaCa-2 cells. There was no significant difference in morphology, growth rate, and sensitivity to PRX321 between parent and GFP-transfected cells (data not shown). GFP-transfected MIA-PaCa-2 tumor chunks were orthotopically transplanted to pancreas of nude mice. These tumor pieces were derived from MIA-PaCa-2-GFP cells transplanted s.c. GFP fluorescence enabled real-time and sequential whole-body imaging of tumors. Noninvasive quantitative measurements of external visible fluorescent area enabled the construction of in vivo tumor growth curves, which seem to correlate with visible tumor growth (see FIGS. 2A and 3A).

Example 5

Complete Eradication of Tumors by Combination of PRX321 and Gemcitabine in an Early Tumor Model Small primary tumor lesions on day 4 after transplantation were observed in all mice by the real-time whole-body imaging (average fluorescent area 26.17 F 4.19 mm2). Treatment was initiated on day 5 after transplantation. Group 1 animals (negative control) did not receive any treatment. Group 2 animals received gemcitabine (150 mg/kg) by i.p. administration twice a week as long as the experiment lasted. Group 3 animals received PRX321 (100 ug/kg by i.p. route twice a day for 5 days. Group 4 animals were treated with the combination of gemcitabine and PRX321. The results are shown in FIG. 2A. Imaging studies on days 14 and 24 confirmed the significant primary tumor growth and metastasis in the non-treatment group. In contrast, gemcitabine or PRX321 treatment group showed a reduction in the rate of tumor growth, compared with non-treatment group. The PRX321 treatment group showed no tumor lesions in 6 of 10 mice on day 14, although tumor recurred by day 34. Remarkably, the combination treatment group revealed significant suppression of tumor growth of primary tumor lesions. Tumor lesions were undetectable in all 10 mice on day 14. By day 44, 6 of 10 mice showed local recurrence and distant metastasis. The rest of the four mice showed complete eradication of tumor and mice remained tumor-free through day 94 when the experiment was terminated.

Example 6

Figure 2B:
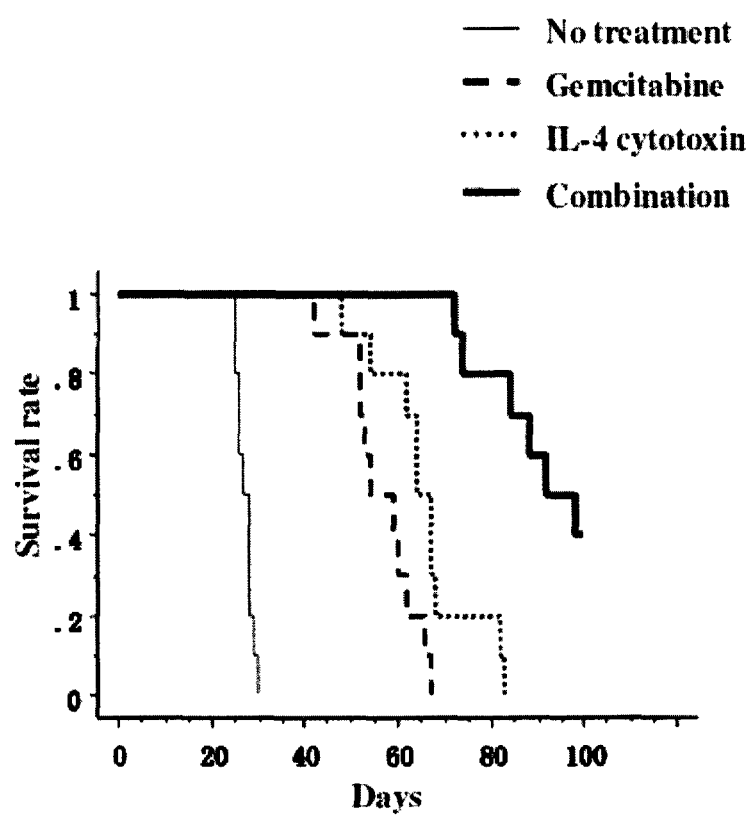
FIG. 2B shows Kaplan-Meier survival curves in an early pancreatic tumor model.

Synergistic Increase in Survival of Mice Treated with a Combination of PRX321 and Gemcitabine in an Early Tumor Model Median survival time of the animals treated in Example 5 was 27 days in non-treatment group, whereas it was significantly increased to 54, 64, and 92 days in gemcitabine group (P<0.0001), PRX321 group (P<0.0001), and their combination group (P<0.0001) compared with non-treatment group, respectively. Compared with gemcitabine group, significant prolonged survival time was observed in PRX321 group (P=0.017) and the combination group (P<0.0001). Increase in significant survival advantage correlated with tumor area as detected by GFP fluorescence. Prolonged survival time in the combination group was 341% compared with the non-treatment group. Kaplan-Meier survival curves are shown in FIG. 2B. In addition, we did not observe any organ toxicity in heart, liver, lung, kidney, and spleen of PRX321-injected mice evaluated by histologic examination.

Example 7

Figure 3A:
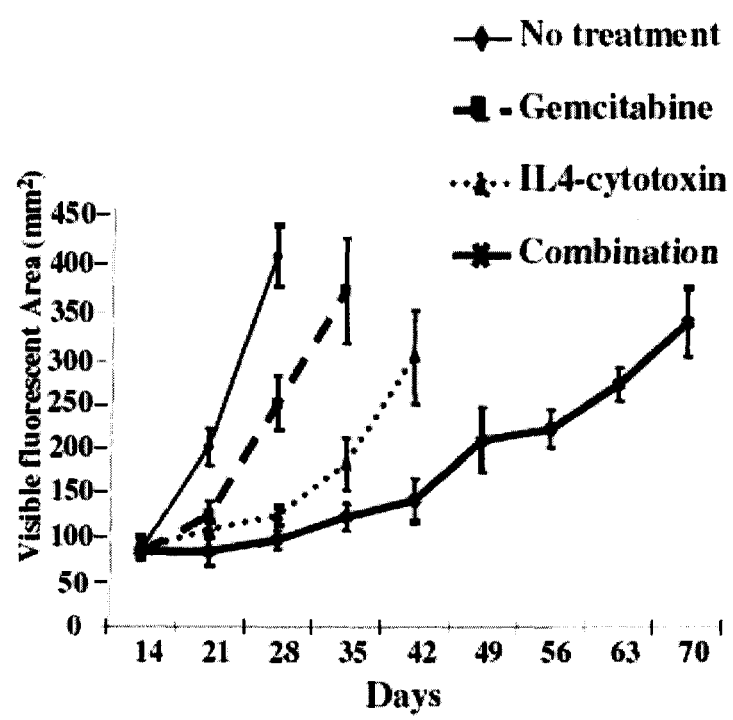
FIG. 3A shows the visible fluorescent area quantification of tumor size as a function of time (obtained from sequential whole-body imaging) in an advanced pancreatic tumor model in which tumor bearing mice received no treatment, treatment with gemcitabine alone, treatment with IL-4 cytotoxin (PRX321) alone, or a combination of gemcitabine and PRX321.

Real-Time Imaging of Tumor Growth of the Primary and Metastasis Lesion in an Advanced In Vivo Model As approximately 85% patients with PDA are diagnosed at an advanced stage at initial diagnosis, an advanced PDA in vivo model needs to be established to imitate the clinical situation and to monitor the disease and treatment effect (33). Fluorescence imaging on day 14 post-transplantation confirmed the tumor growth of primary lesions in all mice and also detected the metastasis lesions to liver, lymph nodes, and peritoneal locations in 40 of 62 mice. Six mice showed metastatic lesions to liver or lymph nodes around hepatoduodenum ligament, 8 showed metastasis lesions corresponding to peritoneal locations, and 26 with both metastasis lesions. We did not include mice with the GFP spot at spleen as a metastasis group. Forty mice with confirmed primary and metastasis tumor lesions on day 14 post-transplantation were divided into four groups and treated as described in Materials and Methods (average fluorescent area 94.67 F 8.31 mm2). Group 1 animals (negative control) did not receive any treatment. Group 2 animals received gemcitabine (150 mg/kg) by i.p. administration twice a week as long as the experiment lasted. Group 3 animals received PRX321 (100 ug/kg by i.p. route twice a day for 5 days. Group 4 animals were treated with the combination of gemcitabine and PRX321. Treatment was done after the confirmation of metastasis lesions on day 14. The results are shown in FIG. 3A. The real-time whole-body imaging of tumor growth confirmed the significant primary tumor growth and metastatic spread on days 14, 21, and 28 after transplantation of tumor in non-treatment control group. Gemcitabine and PRX321 treatment group showed a reduction in the rate of tumor growth compared with the non-treatment group. Especially, the combination treatment group revealed significant suppression of tumor growth at primary and metastasis tumor lesions. The reduction in tumor size on day 28 was 39.8% in the gemcitabine group (P<0.001), 71.2% in the PRX321 group (P<0.001), and 79.6% in the combination group (P<0.001) compared with the no treatment group.

Example 8

Figure 3B:
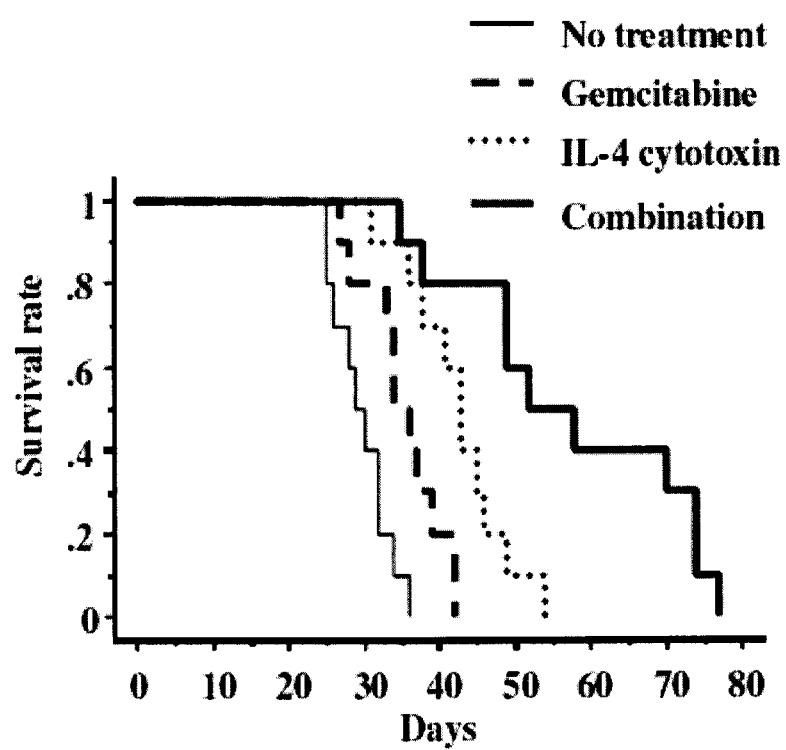
FIG. 3B shows Kaplan-Meier survival curves in an advanced pancreatic tumor model.

Combination of PRX321 and Gemcitabine Prolongs the Survival of Mice with Advanced Orthotopic Pancreatic Tumor We examined the efficacy of PRX321 on the survival of animals in the advanced PDA model in Example 7. Median survival time of animals was 28 days in non-treatment group, whereas it was significantly increased to 34, 43, and 52 days in gemcitabine group (P=0.0089), PRX321 group (P<0.0001), and their combination group (P<0.0001), respectively. Compared with gemcitabine group, significant prolonged survival time was also observed in the PRX321 group (P=0.0047) and the combination group (P=0.0002). Prolonged survival time in the combination group was 186% compared with the non-treatment group. Increase in significant prolongation of survival correlated with tumor area as detected by whole-body imaging. Kaplan Meier survival curves are shown in FIG. 3B.

Example 9

Expression of IL-4R in a Clinical Sample and Development of Orthotopic Xenograft Tumor Model We obtained a tumor tissue sample that was surgically resected at Surgery Branch at NIH and pathologically diagnosed as moderately differentiated adenocarcinom. This tumor section showed strong staining for IL-4Ra in the ductal adenocarcinoma cells and faint staining of fibroblasts. We also established tumor and fibroblast cells cultured from this sample to examine the antitumor activity of PRX321. The cancer cells expressing IL-4R were highly sensitive to PRX321 (IC50 0.32 ng/mL), whereas fibroblast cells were not sensitive (IC50 z1,000 ng/mL;).

Example 10

Figure 4:
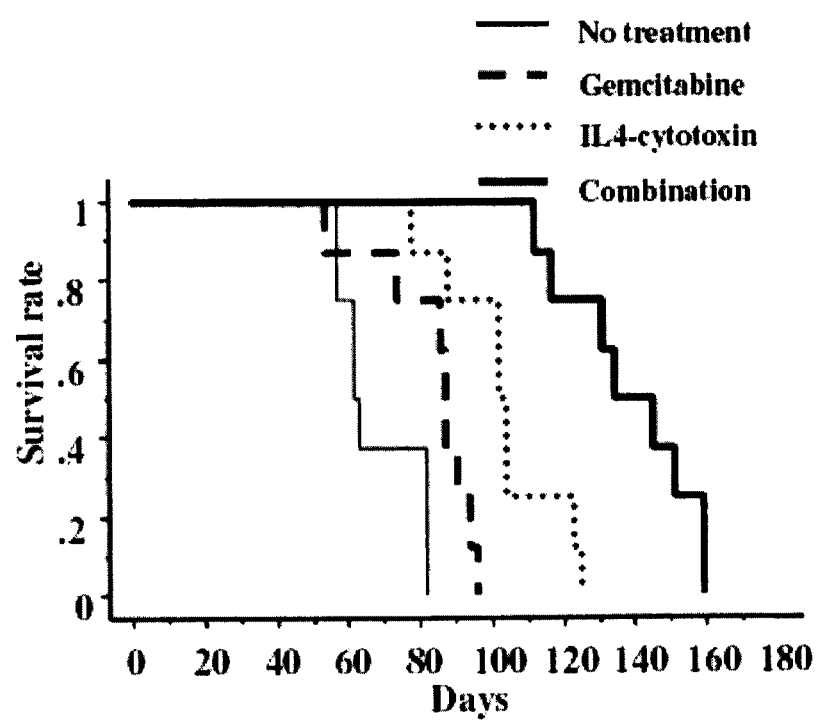
FIG. 4 shows Kaplan-Meyer survival curves in an advanced pancreatic cancer model generated from a clinical sample by orthotopic transplantation in SCID mice.

PRX321, Gemcitabine, and their Combination Significantly Prolonged Survival of Mice Transplanted with a Clinical Pancreatic Cancer Sample The clinical sample described in Example 9 was orthotopically transplanted on the pancreas of SCID mice and when tumors grew, they were harvested and then orthotopically propagated in the next set of SCID mice. All mice showed growth of primary tumor and metastasis to lymph nodes in peritoneum, hepatoduodenum ligament, and para-aortic areas. Seventy-five percent of these mice showed the metastasis lesion to liver when mice were sacrificed 30 days after tumor implantation. To assess the effect of PRX321 in an advanced metastasis model, a third set of SCID mice were orthotopically implanted with tumor pieces obtained from the second set of mice. These mice, when advanced disease developed, were divided into four groups on day 31 and treated as described in Materials and Methods. Group 1 animals (negative control) did not receive any treatment. Group 2 animals received gemcitabine (150 mg/kg) by i.p. administration twice a week as long as the experiment lasted. Group 3 animals received PRX321 (100 ug/kg by i.p. route twice a day for 5 days (days 31-35). Group 4 animals were treated with the combination of gemcitabine and PRX321. Median survival time of animals was 62 days in the non-treatment group, whereas it was significantly increased to 86, 102, and 134 days in the gemcitabine group (P=0.0081), PRX321 group (P=0.0006), and combination group (P<0.0001), respectively. Compared with gemcitabine, significant prolonged survival time was observed of PRX321-treated mice (P=0.0037) and the combination group (P<0.0001). Prolonged survival time in the combination group was 216% compared with the non-treatment group. Kaplan-Meier survival curves are shown in FIG. 4.

Example 11

Conclusions

These studies support our observations of gemcitabine synergizing with PRX321. Despite synergistic effect with gemcitabine, few combinations have shown clinical advantage (4-7). For example, although EGFR inhibitor showed synergistic antitumor effect in preclinical models, the survival benefits for patients with advanced pancreatic cancer seem very modest at best. It was later found that mutations in the EGFR gene, which correlate with clinical response, are found in <5% of pancreatic cancer patients (8, 41). Therefore, new effective therapies that do not depend on receptor mutation are needed. As our results show the survival benefit by PRX321 when combined with gemcitabine in both early and advanced pancreatic cancer models, it is possible that this novel approach will afford better tumor responses than previously observed. The precise mechanism of synergistic effect of gemcitabine with PRX321 is not known. Gemcitabine is a synthetic pyrimidine antimetabolite structurally related to cytarabine (42). Gemcitabine inhibits DNA synthesis through inhibition of ribonucleotide reductase and depletion of deoxynucleotide pools. On the other hand, PRX321 inhibits protein synthesis after internalization into an endosome. In addition, we have previously shown that PRX321 can cause apoptotic cell death of cancer cells regardless of the cell cycle status (43). It is possible that gemcitabine enhances apoptotic cell death induced by PRX321. Because apoptosis is a prominent mechanism of cancer cell death, the combination therapy of these drugs, which act through different mechanism, may be a beneficial treatment option for patients with PDA.

We studied two types of advanced pancreatic cancer models to show the anti-tumor activity of PRX321 and gemcitabine. In orthotopic model, the freshly resected clinical tumor was implanted to pancreas of SCID mice. It has been reported that this model recapitulates the natural history of the clinical disease, including the invasive and metastatic pattern (44). Accordingly, the peritoneal organs, lymph nodes, liver, and spleen of mice in our model showed tumor metastasis and invasion 1 month after transplantation. PRX321 and gemcitabine showed remarkable antitumor effects in this model. In future studies, it will be of interest to determine whether metastatic lesions to various organs express IL-4R, and after treatment with PRX321 these receptor levels decrease along with disappearing tumor. In other orthotopic tumor model, tumor pieces developed from MIPaCa-2-GFP cells by s.c. is implanted to pancreas of nude mice. In this model, PRX321 as well as gemcitabine caused profound antitumor effects. These data are compatible with our previous report that showed the survival benefit by PRX321 alone in orthotopic early and advanced animal models using Panc-1 and BxPC-3 pancreatic cancer cell lines (19). Although we did not test IL-4R-negative tumor in vivo models, our previous studies have shown that non-small cell lung cancer cell line expressing no or low IL-4R are not sensitive to PRX321 in vivo (20). Similar conclusions were drawn in squamous cell carcinoma of head and neck tumor models (45). Thus, PRX321 and gemcitabine show better survival benefit compared with either agent alone in two pancreatic tumor models, one derived from clinical sample and the other derived from MIPaCa-2 cell line.

The whole-body imaging of host visualizes the real-time tumor growth at the primary site and tumor development at metastasis sites without the invasive procedures, surgery, anesthesia, or use of contrast medium. Due to the fact that whole-body imaging has the potential of high correlation with MRI in quantifying tumor volume, the precise evaluation of tumor growth rate, metastatic situation, and effectiveness of drugs could all be monitored without sacrificing animals (32, 46). In addition, imaging may identify biomarker of tumor response in preclinical models that can be validated in the clinical trial (47). A recent article reported that red fluorescent protein showed brighter and less background image compared with GFP, when animals were imaged (48). In our study, we used GFP-transfected cells. Therefore, it is possible that we were not able to detect micrometastasis lesions. Nevertheless, we could show that mice developed spontaneous tumor metastasis within the short time after orthotopic transplantation, which correlated with short survival time. In addition, our model showed that PRX321 reduced the rate of tumor growth, including primary and metastasis lesions for 15 and 9 days after treatment in early and advanced model, respectively.

Although PRX321 mediated remarkable antitumor effects in vivo, no visible signs of toxicity and features such as weight loss and inactivity were observed in mice receiving optimal doses of PRX321 and/or gemcitabine (data not shown). These results are compatible with previous studies related to both agents (data not shown; refs. 19, 24, 49). Previous studies have shown that low density IL-4R are expressed on normal immunologic and nonhematopoietic cells (22). Consequently, PRX321 is not cytotoxic to these cells. Preclinical toxicity studies in mice have shown that PRX321 is well tolerated up to 475 Ag/kg dose given i.v. (50). As human IL-4 does not bind murine IL-4R, PRX321 has also been administered to cynomolgus monkeys, whose IL-4R binds human IL-4. In these animals, PRX321 was reasonably tolerated up to a dose of 200 Ag/kg given i.v. every alternate day for three injections (21). In a phase 1 clinical trial, reversible elevation of liver enzymes and injection site inflammatory reactions were reported after i.v. administration of PRX321 at 0.027 mg/m2 (25). As our study shows synergistic effects when PRX321 is combined with gemcitabine against pancreatic cancer in vitro and in vivo, lower doses of PRX321 may be effective for the treatment of patients with PDA when combined with gemcitabine.

In conclusion, these studies provide a novel approach for monitoring tumor response by whole-body imaging of the host. Further studies should be done to evaluate the safety, tolerability, and efficacy of PRX321 when combined with gemcitabine in various pancreatic cancer models. In addition, because of their synergistic effect, PRX321 in combination with gemcitabine should be tested in patients with PDA.

Example 12

Repetitive Therapy of Orthotopic Human Pancreatic Cancer by of IL4-PE

Immunodeficient nude mice were transplanted with Green Fluorescence Protein (GFP) transfected human pancreatic tumor cells (Hs766T) orthotropically on pancreas. Five days after tumor implantation, mice were treated with IL4-PE 100 ug/kg/day, i.p. for one week or every alternate week for 3 weeks. Tumor size was measured by imaging of visible fluorescence area in live animals.

One week administration of IL-4-PE significantly decreased the tumor volume compared to control. However, repetitive therapy with IL4-PE caused dramatic regression of established pancreatic tumor growth. We did not observe any visible side effects with repetitive therapy of IL4-PE.

REFERENCES

1. Sener S F, Fremgen A, Menck H R, Winchester D P. J Am Coll Surg 1999; 189:1-7.
2. Tempero M, Plunkett W, Ruiz Van Haperen V, et al. J Clin Oncol 2003; 21:3402-8.
3. Burris H A, Moore M J, Andersen J, et al. J Clin Oncol 1997; 15:2403-13.
4. Bruns C J, Solorzano C C, Harbison M T, et al. Cancer Res 2000; 60:2926-35.
5. Yokoi K, Sasaki T, Bucana C D, et al. Cancer Res 2005; 65:10371-80.
6. Bergers G, Song S, Meyer-Morse N, Bergsland E, Hanahan D. J Clin Invest 2003; 111:1287-95.
7. Fujioka S, Sclabas G M, Schmidt C, et al. Oncogene 2003; 22:1365-70.
8. Moore M J, Goldstein J, Hamm A, et al. J Clin Oncol. 2005 ASCO Annual Meeting Proceedings. Vol 23, No. 16S, Part I of II (June 1 Supplement); 2005:1.
9. Pastan I, Hassan R, Fitzgerald D J, Kreitman R J. Nat Rev Cancer 2006; 6:559-65.

10. Rand R W, Kreitman R J, Patronas N, Varricchio F, Pastan I, Puri R K. Clin Cancer Res 2000; 6:2157-65.
11. Weber F, Asher A, Bucholz R, et al. J Neurooncol 2003; 64:125-37.
12. Kioi M, Husain S R, Croteau D, Kunwar S, Puri R K. Technol Cancer Res Treat 2006; 5:239-50.
13. Kreitman R J, Squires D R, Stetler-Stevenson M, et al. J Clin Oncol 2005; 23:6719-29.
14. Nelms K, Keegan A D, Zamorano J, Ryan J J, Paul W E. Annu Rev Immunol 1999; 17:701-38.
15. Toi M, Bicknell R, Harris A L. Cancer Res 1992; 52:275-9.
16. Topp M S, Papadimitriou C A, Eitelbach F, et al., Cancer Res 1995; 55:2173-6.
17. Stadler W M, Rybak M E, Vogelzang N J. Cancer 1995; 76:1629-33.
18. Husain S R, Kreitman R J, Pastan I, Puri R K. Nat Med 1999; 5:817-22.
19. Kawakami K, Kawakami M, Husain S R, Puri R K. Cancer Res 2002; 62:3575-80.
20. Kawakami M, Kawakami K, Stepensky V A, et al. Clin Cancer Res 2002; 8:3503-11.
21. Kawakami M, Kawakami K, Puri R K. J Neurooncol 2003; 65:15-25.
22. Kawakami K, Kawakami M, Puri R K. Crit Rev Immunol 2001; 21:299-310.
23. Kreitman R J, Puri R K, Pastan I. Proc Natl Acad Sci USA 1994; 91:6889-93.
24. Kioi M, Takahashi S, Kawakami M, Kawakami K, Kreitman R J, Puri R K. Cancer Res 2005; 65:8388-96.
25. Garland L, Gitlitz B, Ebbinghaus S, et al. J Immunother 2005; 28:376-81.
26. Rainov N G, Heidecke V. J Neurooncol 2004; 66:197-201.
27. Hoffman R M. Nat Rev Cancer 2005; 10:796-806.
28. Furukawa T, Duguid W P, Rosenberg L, Viallet J, Galloway D A, Tsao M S. 16. Am J Pathol 1996; 148: 1763-70.
29. Puri R K, Leland P, Kreitman R J, Pastan I. Int J Cancer 1994; 58:574-81.
30. Chou T C, Motzer R, Tong Y, Bosl G. J Natl Cancer Inst 1994; 86:1517-24.
31. Murata T, Obiri N I, Debinski W, Puri R K. Biochem Biophys Res Commun 1997; 238:90-4.
32. Bouvet M, Wang J, Nardin S R, et al. Cancer Res 2002; 62:1534-40.
33. Abbruzzese J L. Semin Oncol 2002; 29:2-8.
34. Symon Z, Davis M, McGinn C J, Zalupski M M, Lawrence T S. Int J Radiat Oncol Biol Phys 2002; 53:140-5.
35. Bocci G, Fioravanti A, Orlandi P, et al. Br J Cancer 2005; 93:319-30.
36. Pratesi G, Petrangolini G, Tortoreto M, et al. Cancer Res 2005; 65:6388-93.
37. Chun P Y, Feng F Y, Scheurer A M, et al. Cancer Res 2006; 66:981-8.
38. O'Connor R, Liu C, Ferris C A, et al. Blood 1995; 86:4286-94.
39. Kim C N, Bhalla K, Kreitman R J, et al. Leuk Res 1999; 23:527-38.
40. Polito L, Bolognesi A, Tazzari P L, et al. Leukemia 2004; 18:1215-22.
41. Gilbert J A, Lloyd R V, Ames M M. N Engl J Med 2005; 353:209-10.
42. Morgan A. Highlights Oncol Pract 1996; 14:74-9.
43. Husain S R, Kawakami K, Kawakami M, Puri R K. Mol Cancer Ther 2003; 2: 245-54.
44. Manzotti C, Audisio R A, Pratesi G. Clin Exp Metastasis 1993; 11:5-14.
45. Strome S E, Kawakami K, Alejandro D, et al. Clin Cancer Res 2002; 8:281-6.
46. Bouvet M, Spernyak J, Katz M H, et al. Cancer Res 2005; 65:9829-33.
47. Saur D, Seidler B, Schneider G, et al. Gastroenterology 2005; 129:1237-50.
48. Katz M H, Takimoto S, Spivack D, Moossa A R, Hoffman R M, Bouvet M. J Surg Res 2003; 113:151-60.
49. Zhang X, Galardi E, Duquette M, Lawler J, Parangi S. Clin Cancer Res 2005; 11:5622-30.
50. Puri R K, Hoon D S, Leland P, et al. Cancer Res 1996; 56:5631-7.

I claim:

1. A method of inhibiting a cancer cell that overexpresses an IL-4 receptor, comprising:
   a. contacting said cancer cell with a targeted cargo protein PRX321 comprising a targeting moiety that specifically binds to an IL-4 receptor, and a cargo moiety that inhibits said cancer cell, and
   b. contacting said cancer cell with an active anti-cancer agent.

2. The method of claim 1, wherein said cancer cell is a cell of a cancer selected from the group consisting of brain cancer, a hematological cancer, Kaposi sarcoma, bladder cancer, renal cell cancer, breast cancer, pancreatic cancer, non-small cell lung cancer, thyroid cancer, squamous cell carcinoma of the head and neck, colon cancer, bile duct carcinoma, ovarian cancer, a cancer of the gastrointestinal system, mesothelioma, rhabdomyosarcoma, and prostate cancer.

3. The method of claim 1, wherein said cancer cell is selected from the group consisting of a malignant astrocytoma cell, a medulloblastoma cell, a meningioma cell, and a glioma cell.

4. The method of claim 1, wherein said active anti-cancer agent is selected from the group consisting of gemcitabine, doxorubicin, FOLFOX (folinic acid, fluorouracil, and oxaliplatin), premetrexed, irinotecan, temozolamide, cisplatin, oxaliplatin, erlotinib, imatinib, cetuximab, bevacizumab, and rituximab, and an antibody or other active agent used to treat cancer.

\* \* \* \* \*

SEQUENCE LISTING

```
<160> NUMBER OF SEQ ID NOS: 1

<210> SEQ ID NO 1
<211> LENGTH: 485
<212> TYPE: PRT
<213> ORGANISM: Artificial Sequence
<220> FEATURE:
<223> OTHER INFORMATION: a circularly permuted IL-4-Pseudomonas toxin,
      PRX321

<400> SEQUENCE: 1

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Leu Arg Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80
```

-continued

Lys Thr Ile Met Arg Glu Lys Tyr Ser Lys Cys Ser Ser Gly Gly Asn
                85                  90                  95
Gly Gly His Lys Cys Asp Ile Thr Leu Gln Glu Ile Ile Lys Thr Leu
            100                 105                 110
Asn Ser Leu Thr Glu Gln Lys Thr Leu Cys Thr Glu Leu Thr Val Thr
        115                 120                 125
Asp Ile Phe Ala Ala Ser Lys Ala Ser Gly Gly Pro Glu Gly Gly Ser
    130                 135                 140
Leu Ala Ala Leu Thr Ala His Gln Ala Cys His Leu Pro Leu Glu Thr
145                 150                 155                 160
Phe Thr Arg His Arg Gln Pro Arg Gly Trp Glu Gln Leu Glu Gln Cys
                165                 170                 175
Gly Tyr Pro Val Gln Arg Leu Val Ala Leu Tyr Leu Ala Ala Arg Leu
            180                 185                 190
Ser Trp Asn Gln Val Asp Gln Val Ile Arg Asn Ala Leu Ala Ser Pro
        195                 200                 205
Gly Ser Gly Gly Asp Leu Gly Glu Ala Ile Arg Glu Gln Pro Glu Gln
    210                 215                 220
Ala Arg Leu Ala Leu Thr Leu Ala Ala Ala Glu Ser Glu Arg Phe Val
225                 230                 235                 240
Arg Gln Gly Thr Gly Asn Asp Glu Ala Gly Ala Ala Asn Gly Pro Ala
                245                 250                 255
Asp Ser Gly Asp Ala Leu Leu Glu Arg Asn Tyr Pro Thr Gly Ala Glu
            260                 265                 270
Phe Leu Gly Asp Gly Gly Asp Val Ser Phe Ser Thr Arg Gly Thr Gln
        275                 280                 285
Asn Trp Thr Val Glu Arg Leu Leu Gln Ala His Arg Gln Leu Glu Glu
    290                 295                 300
Arg Gly Tyr Val Phe Val Gly Tyr His Gly Thr Phe Leu Glu Ala Ala
305                 310                 315                 320
Gln Ser Ile Val Phe Gly Val Arg Ala Arg Ser Gln Asp Leu Asp
                325                 330                 335
Ala Ile Trp Arg Gly Phe Tyr Ile Ala Gly Asp Pro Ala Leu Ala Tyr
            340                 345                 350
Gly Tyr Ala Gln Asp Gln Glu Pro Asp Ala Arg Gly Arg Ile Arg Asn
        355                 360                 365
Gly Ala Leu Leu Arg Val Tyr Val Pro Arg Ser Ser Leu Pro Gly Phe
    370                 375                 380
Tyr Arg Thr Ser Leu Thr Leu Ala Ala Pro Glu Ala Ala Gly Glu Val
385                 390                 395                 400
Glu Arg Leu Ile Gly His Pro Leu Pro Leu Arg Leu Asp Ala Ile Thr
                405                 410                 415
Gly Pro Glu Glu Glu Gly Gly Arg Leu Glu Thr Ile Leu Gly Trp Pro
            420                 425                 430
Leu Ala Glu Arg Thr Val Val Ile Pro Ser Ala Ile Pro Thr Asp Pro
        435                 440                 445
Arg Asn Val Gly Gly Asp Leu Asp Pro Ser Ser Ile Pro Asp Lys Glu
    450                 455                 460
Gln Ala Ile Ser Ala Leu Pro Asp Tyr Ala Ser Gln Pro Gly Lys Pro
465                 470                 475                 480
Pro Lys Asp Glu Leu
                485